(12) United States Patent
Zhu

(10) Patent No.: US 11,096,719 B2
(45) Date of Patent: Aug. 24, 2021

(54) OPTICAL BLADELESS OBTURATOR

(71) Applicant: 5RMED TECHNOLOGY (CHENGDU) CO., LTD, Sichuan (CN)

(72) Inventor: Moshu Zhu, Sichuan (CN)

(73) Assignee: 5RMED TECHNOLOGY (CHENGDU) CO., LTD, Chengdu (CN)

( * ) Notice: Subject to any disclaimer, the term of this patent is extended or adjusted under 35 U.S.C. 154(b) by 207 days.

(21) Appl. No.: 16/435,343

(22) Filed: Jun. 7, 2019

(65) Prior Publication Data

US 2019/0290321 A1 Sep. 26, 2019

Related U.S. Application Data

(63) Continuation of application No. PCT/CN2017/113715, filed on Nov. 30, 2017.

(30) Foreign Application Priority Data

Dec. 9, 2016 (CN) .......................... 201611125444.3

(51) Int. Cl.
*A61B 17/34* (2006.01)
*A61B 90/00* (2016.01)
*A61B 17/00* (2006.01)

(52) U.S. Cl.
CPC ...... *A61B 17/3421* (2013.01); *A61B 17/3417* (2013.01); *A61B 17/3478* (2013.01);
(Continued)

(58) Field of Classification Search
CPC . A61B 17/34; A61B 17/3415; A61B 17/3417; A61B 17/3421; A61B 17/3423;
(Continued)

(56) References Cited

U.S. PATENT DOCUMENTS

| | | | | |
|---|---|---|---|---|
| 2002/0133188 | A1* | 9/2002 | O'Heeron | A61B 17/3417 606/185 |
| 2005/0065543 | A1* | 3/2005 | Kahle | A61B 90/92 606/190 |

(Continued)

FOREIGN PATENT DOCUMENTS

| | | |
|---|---|---|
| CN | 1441683 A | 9/2003 |
| CN | 103083068 A | 5/2013 |

(Continued)

*Primary Examiner* — Robert A Lynch

(57) ABSTRACT

An improved transparent bladeless obturator includes a proximal handle, a distal-end portion and a shaft therebetween, the handle and the shaft including a generally-aligned axis aperture, the distal-end portion including a transparent tip, from the distal end to the proximal end, the transparent tip divided into a top-portion, a spear-portion, a transition-portion and a base-portion; the top-portion includes an apex and a rotary-wall extending axially from the apex to the proximal end and gradually increasing in a transverse direction, the rotary-wall limiting a hollow cone; the main-portion including a main-body wall, the rotary-wall and the main-body wall extend to be intersected and form a circular field of vision; the sweeping-wall extends axially from the distal end to the proximal end and gradually increases in a transverse direction; and the spear-portion includes the first transverse-portion and the second transverse-portion.

12 Claims, 24 Drawing Sheets

(52) U.S. Cl.
CPC ............... *A61B 17/3494* (2013.01); *A61B 2017/00902* (2013.01); *A61B 2017/3419* (2013.01); *A61B 2017/3454* (2013.01); *A61B 2090/0801* (2016.02)

(58) Field of Classification Search
CPC .......... A61B 2017/00902; A61B 2017/00907; A61B 2017/320044; A61B 2017/3454; A61B 2017/3456; A61B 2017/346
See application file for complete search history.

(56) References Cited

U.S. PATENT DOCUMENTS

| | | | | |
|---|---|---|---|---|
| 2005/0107816 | A1* | 5/2005 | Pingleton | ............... A61B 17/02 606/185 |
| 2009/0204140 | A1 | 8/2009 | Dandl et al. | |
| 2012/0071909 | A1* | 3/2012 | Fischvogt | .......... A61B 17/3496 606/190 |
| 2014/0249371 | A1* | 9/2014 | Fischvogt | ............ A61B 1/3132 600/114 |

FOREIGN PATENT DOCUMENTS

| | | | |
|---|---|---|---|
| CN | 203710097 | U | 7/2014 |
| CN | 105769301 | A | 7/2016 |
| CN | 106510809 | A | 3/2017 |
| CN | 206714801 | U | 12/2017 |

\* cited by examiner

OPTICAL BLADELESS OBTURATOR

CROSS-REFERENCE TO RELATED APPLICATIONS

This application is a continuation of International Patent Application No. PCT/CN2017/113715, filed on Nov. 30, 2017, which claims priority to Chinese Patent Application No. 201611125444.3, filed on Dec. 9, 2016. The content of the aforementioned applications, including any intervening amendments thereto, are incorporated herein by reference.

TECHNICAL FIELD

The present application relates to a minimally invasive surgical instrument, and in particular, to a trocar obturator.

BACKGROUND

A trocar is a surgical instrument that is used to establish an artificial access in minimally invasive surgery (especially in rigid endoscopy). A trocar assembly generally comprise in general a cannula and an obturator. Usually, limiting the side that is the obturator and the cannula close to the handle of the surgeon is proximal end, the side that is away from the hand and preferentially penetrates the body cavity is the distal end. The general clinical use is as follows: firstly cut a small incision on the patient's skin, and then pass the obturator through the cannula, the distal end of the obturator exceeds the distal end of the cannula, and then through the skin opening penetrating the body wall into the body cavity.

During penetration, the surgeon holds the trocar and applies a large penetration force to overcome the resistance to penetrating and cutting the tissue, as well as the resistance to expansion and swelling of the tissue. The distal end of the obturator usually contains a sharp blade that helps reduce the penetration force and the cutting-tissue force. At the moment of penetrating the body wall, the resistance suddenly disappears, and the surgeon may not be able to stop applying force or due to inertia, so the blade may accidentally damage the interior tissue of the patient. Therefore, the obturator usually includes a selective-axial-moved protective shield and an automatic lock device, which is called an automatic protective obturator with blade (hereinafter referred to as a protective obturator). At the moment of penetrating the body wall, the automatic lock device is triggered almost simultaneously, and the protective shield is moved almost instantaneously to the distal end covering blade and locked, thereby preventing the blade from being exposed to cause damage.

Even under the effective protection of the shield, due to the surgeon lack of experience or failure to stop applying the penetration force in time, the protective shield contacts the patient's interior organs or tissues in an impact manner, which may still cause varying degrees of unpredictable damage. For reducing the risk of damage to interior organs, in the clinical application, when the surgeon holds trocar for penetration, the manner of penetrating into the body is rotating back and forth in a small range instead of a simple linear motion. The round-trip rotary manner is beneficial for tearing and swelling muscle tissue, and for controlling the penetration speed and reducing the aforementioned inertia effect. While in this the round-trip rotary manner, the blade of the protective obturator rotates back and forth and cuts muscle tissue, resulting in irregular wounds, thereby additionally increasing the damage to the patient, and increasing the occurrence probability of incision hernia complication.

Studies have shown that the obturator without blade (hereinafter referred to as the bladeless obturator) is beneficial for reducing damage to the patient. When penetrating the body wall with the bladeless obturator, the distal end of the bladeless obturator penetrates the muscle and tissue due to the absence of a sharp blade, separates the muscle fiber and swells the wound until the obturator and the cannula assembly passing through the body wall. Compared with the protective obturator, the bladeless obturator reduces the cutting damage to the muscle tissue, helps the postoperative recovery, and helps reducing the probability of incision hernia complication. However, when the obturator is used for penetration, the penetration force is generally larger than which of protective obturator, so it is more difficult to control, and the risk of damage to organs and tissues for the patient is increased.

U.S. Pat. No. 5,569,292 discloses a transparent bladeless obturator comprising an elongate shaft and a transparent conical penetrating tip. When using the transparent bladeless obturator, the endoscope is inserted into the hollow shaft. The endoscope is connected to a light source to provide illumination through the transparent penetrating tip and tissue wrapped in the outer surface of the transparent tip. It is also connected to a video monitor to display the illuminated images transmitted from the surgical site. In this way, the user can readily monitor the advance of trocar through bodily tissue from video. Following U.S. Pat. No. 5,569,292, different inventors have successively disclosed a variety of improved transparent bladeless obturators that optimize the performance of the transparent bladeless obturator from different perspectives. So far, the transparent bladeless penetration has been commercialized and used in a large number of clinical applications. However, there is still some problem that the transparent bladeless trocar needs to be improved continually. For example, the transparent bladeless obturator used in conjunction with the endoscope is inconvenient to handle, so that it is urgent to reduce the penetration force to a greater extent, thereby improving the penetration controllability and efficiency. For example, greater improving the transparency of the transparent penetrating tip is for a clearer image.

In order to solve the problem or several problems descried above, the present invention proposes an improved transparent bladeless obturator.

SUMMARY

In conclusion, one object of the invention is to provide an improved optical bladeless obturator.

In one aspect of the invention, an optical bladeless obturator comprises a proximal handle and a distal-end portion and a shaft there between, said handle and said shaft including a generally-aligned axis aperture, said distal-end portion including a transparent tip. Said transparent tip comprising a top-portion, a spear-portion, a transition-portion and a base-portion. The top-portion includes an apex and a rotary-wall extending axially from the apex to the proximal end and gradually increasing in a transverse direction, the rotary-wall shaping a hollow cone; the spear-portion including a sweeping-wall, the rotary-wall and the sweeping-wall extend to be intersected and form a circular field of vision. The circular field of vision facilitates clearer imaging and less distortion of the apex and its adjacent region.

The sweeping-wall extends axially from the distal end to the proximal end and gradually increases in a transverse direction. The spear-portion includes the first transverse-portion and the second transverse-portion that are substantially perpendicular to each other, and the dimension of the first transverse-portion is greater than the dimension of the second transverse-portion. The transverse dimension ratio of the first transverse-portion and the second transverse-portion is gradually reduce from the distal end to the proximal end. In an optional embodiment, the cross section of the spear-portion is an elliptical-shape. In another optional embodiment, the cross section of the spear-portion is approximately an elliptical polygon. When the top-portion is inserted into the muscle or tissue, the spear-portion is advantageous in reducing the total amount of the muscle which is simultaneously torn and swelled, thereby contributing to reducing the penetration force.

Optionally, the size of the circular field of vision conforms to the following equation:

$$2\ mm \leq D \leq 0.5D0,$$

wherein:

D=diameter of the circular field of view,

D0=the maximum outer diameter of the distal-end portion of the obturator.

In another aspect of the invention, an obturator comprises a proximal handle and a distal-end portion and a shaft there between, said handle and said shaft including a generally-aligned axis aperture, said distal-end portion including a transparent tip. From the distal end to the proximal end, said transparent tip is divided into a top-portion, a spear-portion, a main-portion and a base-portion. The top-portion includes an apex and a rotary-wall extending axially from the apex to the proximal end and gradually increasing in a transverse direction, the rotary-wall shaping a hollow cone; the main-portion including a main-body wall, the rotary-wall and the main-body extend to be intersected and form a circular field of vision. The main-body wall extends axially from the distal end toward the proximal end and gradually increases in a transverse direction, and the thickness of the rotary-wall is smaller than the wall thickness of the main-body wall. The thinner the thickness of the top-portion, the more advantageous it is to reduce light loss and obtain a clearer image.

In another aspect of the invention, an obturator comprises a proximal handle and a distal-end portion and a shaft there between, said handle and said shaft including a generally-aligned axis aperture, said distal-end portion including a transparent tip. From the distal end to the proximal end, said transparent tip is divided into a top-portion, a spear-portion, a transition-portion and a base-portion. The top-portion includes an apex and a rotary-wall extending axially from the apex to the proximal end and gradually increasing in a transverse direction, the rotary-wall limiting a hollow cone. The spear-portion includes a sweeping-wall, which extends axially from the distal end to the proximal end and gradually increases in a transverse direction. The spear-portion includes the first transverse-portion and the second transverse-portion that are substantially perpendicular to each other, and the dimension of the first transverse-portion is larger than the dimension of the second transverse-portion. The first transverse-portion extends transversely to form a blunt-separating portion. The transparent tip includes at least one thin working-edge, the working-edge extends transversely outward from the second transverse-portion, the working-edge substantially perpendicular to the first transverse-portion.

In an optional embodiment, the rotary-wall and the sweeping-wall extend to be intersected and form a circular field of vision. In another optional embodiment, the cross section of the spear-portion is an oval-shape or approximately an oval-polygon. In another optional embodiment, the transition-portion includes the first transverse-portion and the second transverse-portion that are substantially perpendicular to each other, and a transverse dimension of the first transverse-portion is greater than the dimension of the second transverse-portion, which is asymmetrical, that is, the half of the second transverse-portion has a larger dimension than the other half of it. In another optional embodiment, the transparent tip includes two working-blades.

Another object of the invention is to provide a trocar, which comprises a cannula and a optical obturator.

BRIEF DESCRIPTION OF THE DRAWINGS

A more complete appreciation of this invention, and many of the attendant advantages thereof will be readily apparent as the same becomes better understood by reference to the following detailed description, where.

In all views, the same referred number shows the same element or assembly.

DETAILED DESCRIPTION OF EMBODIMENTS

Embodiments of the invention are disclosed herein, however, it should be understood that the disclosed embodiments are merely examples of the invention, which may be implemented in different ways. Therefore, the invention is not intended to be limited to the detail shown, rather, it is only considered as the basis of the claims and the basis for teaching those skilled in the art how to use the invention.

Figure 1:
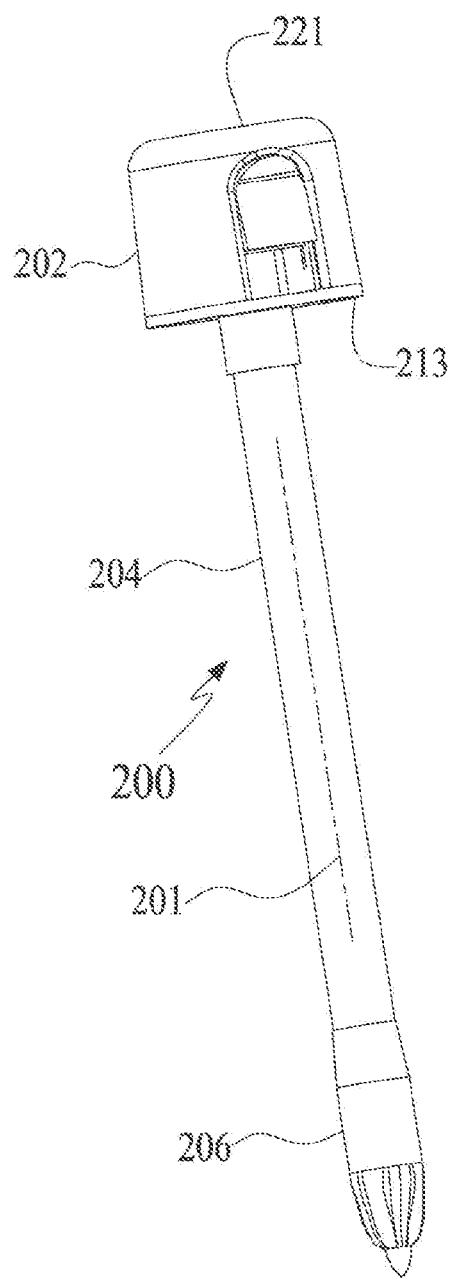
FIG. 1 is a 3D perspective view of trocar assembly.
Figure 2:
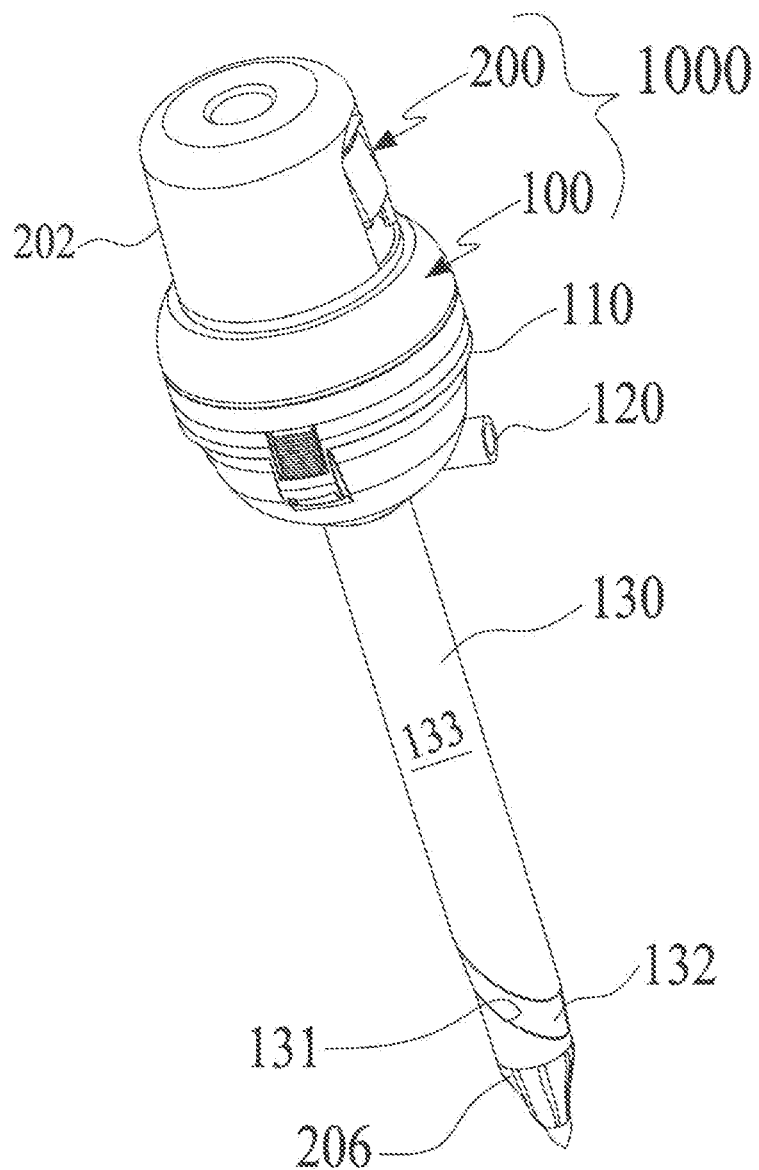
FIG. 2 is a 3D perspective view of the obturator in the first embodiment of the invention.

FIG. 1-2 illustrate the structure of the trocar 1000. A trocar 1000 comprises the cannula 100 and the obturator 200, the cannula 100 including a seal housing 110, a valve 120, and a sleeve 130. The seal housing 110 comprises a cannula top-surface 111 (not shown) and a hollow aperture 113 (not shown). In general, the duckbill seal (also known as closure valve) and a seal membrane (also known as instrument seal) are in turn secured in the seal housing 110 from the distal end to the proximal end. Said duckbill seal normally does not provide sealing for the inserted instrument, but automatically closing and forming a seal when the instrument is removed; said seal membrane accomplishes a gas-tight seal against the instrument when it is inserted. The sleeve 130 includes an open sleeve-distal-end 132 and a hollow shaft 133 that connected with the seal housing 110, the sleeve-distal-end 132 including a sleeve-lip 131. The obturator 200 is composed of a handle 202, a shaft 204 and the distal-end portion 206. The handle includes a top-wall 221 and a handle bottom-surface 213.

Referring to FIG. 1-2, the obturator 200 passes through the cannula 100, and the cannula top-surface 111 is connected with the handle bottom-surface 213. When the penetration is performed, the surgeon grips the seal housing 110, and the palm rests against the top-wall 221 of the handle, continuously applying a penetration force to penetrate the patient's body wall. Once penetrated into the body cavity, the obturator is removed, and the cannula will be left as access for the instrument get in/out of the body cavity. For convenience of description, in the following the portion close to the surgeon is limited as the proximal end, and the portion far from the surgeon is limited as the distal end. The central axis of the obturator shaft 204 is limited as the axis 201. The direction substantially parallel to the axis 201 is referred to be the axial direction and the direction substantially perpendicular to the axis 201 is referred to the transverse direction.

Figure 3:
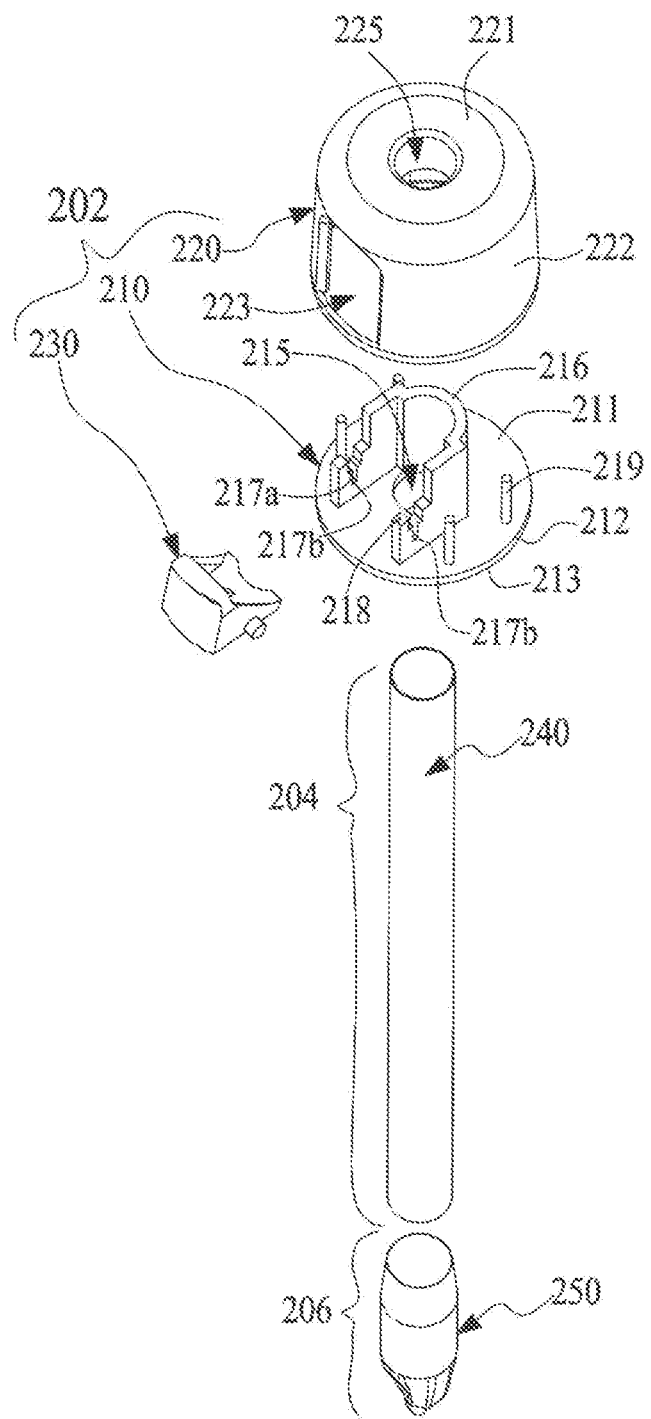
FIG. 3 is a 3D perspective view of the obturator in FIG. 2.

FIGS. 2-9 show detailed depiction the first embodiment in the invention, the composition and assembly relationship of the transparent bladeless obturator 200. The obturator used in endoscopic surgery can be generally divided into two major categories: a blade obturator and a bladeless obturator. The "blade" refers to a metal-blade, and the "bladeless" refers to a metal-free blade. An obturator with a plastic blade is often referred to as a bladeless obturator, which is the convention in the art. Referring to FIG. 2-3, the handle 202 includes a handle base 210, a handle housing 220 and a cam lock 230, said shaft 204 including the elongate shaft 240, said distal-end portion 206 including the transparent tip 250.

Figure 7:
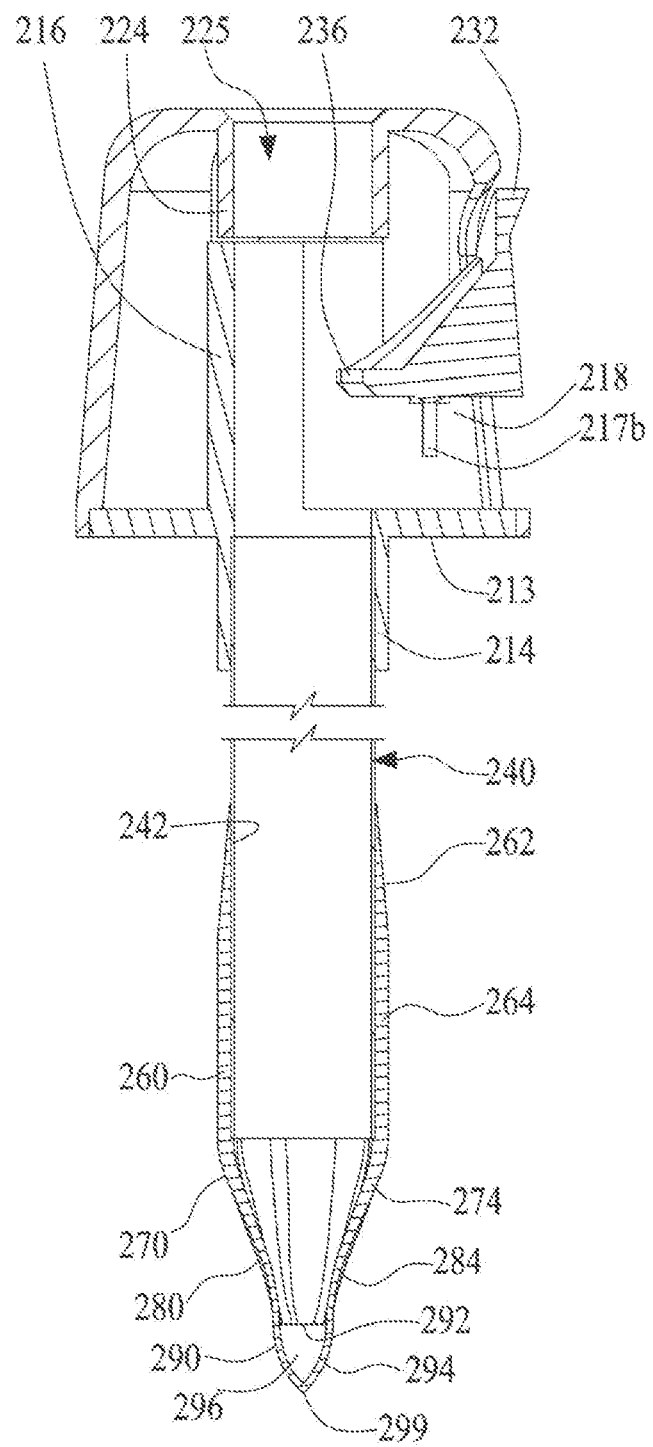
FIG. 7 is a cross-section view taken along line 7-7 of FIG. 6.

Referring to FIG. 3 and FIG. 7, the handle base 210 includes a flange 212, which comprises handle top-surface 211 is connected with the handle bottom-surface 213. The elongated shaft 214s include hollow aperture 215 and extends from the handle bottom-surface 213 to the distal end. The U-shaped guide wall 216 extends from the handle top-surface 211 to the proximal end. The guide wall 216 include a lock retainer-recess 217a and a deformation-recess 217b, wherein the lock retainer-recess 217a and the deformation-recess 217b divide the cantilever 218 and the guide wall 216 apart. The flange further includes a plurality of retainer-pins 219.

Figure 4:
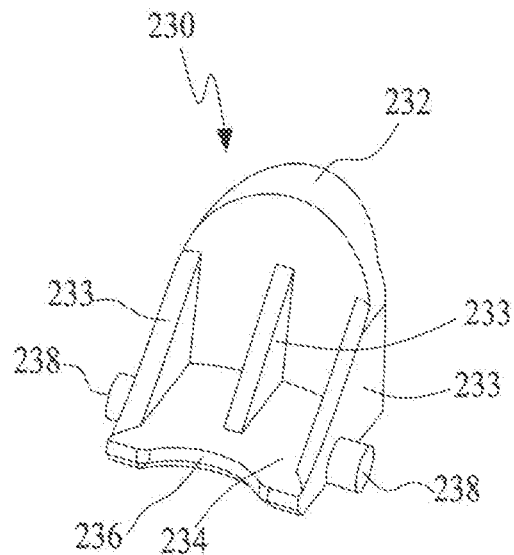
FIG. 4 is a 3D perspective view of the cam lock in FIG. 3.
Figure 5:
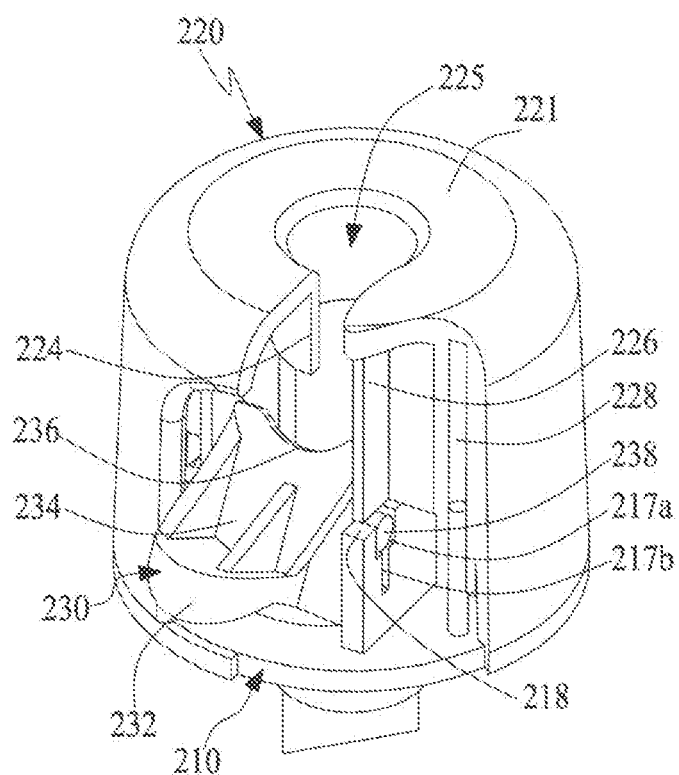
FIG. 5: shows a partial-section view of the obturator of the handle-portion in FIG. 2.

Referring to FIGS. 3-4, the cam lock 230 includes a proximal wrench 232 and a connected distal cam 234, which includes a cam lip 236. A plurality of reinforcing ribs 233 simultaneously are connected with the proximal wrench 232 and the distal cam 234. The cam lock 230 further includes a rotary-shaft 238 extending transversely outward from the reinforcing rib 233. Referring to FIG. 3 and FIG. 5, the handle housing 220 includes a handle top-wall 221 and a connected handle sidewall 222, which includes a side aperture 223. The handle housing 220 further includes a guide aperture 225 formed by a guide cylinder 224. A plurality of limit ribs 226 and hollow retainer-pins 228 are connected with the handle top-wall 221 and extend toward the distal end.

Figure 6:
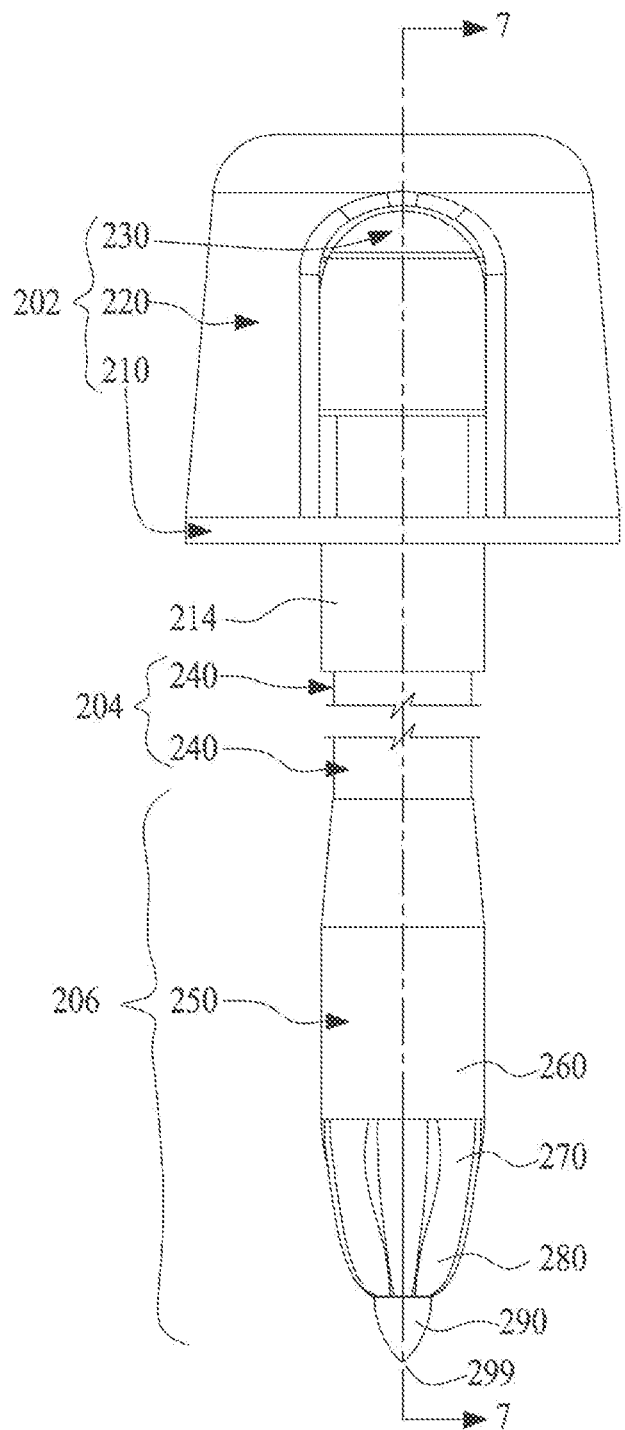
FIG. 6 is a front projection view of the obturator in FIG. 2.

Referring to FIGS. 5-7, the cam lock 230 is mounted to the handle base 210, wherein the rotary-shaft 238 is matched with the lock retainer-recess 217a. Those skilled in the art can appreciate that the handle housing 220 and the handle base 210 can be secured together by a variety of well-known joining techniques, such as bonding, welding, mechanical securing, and so on. In the present embodiment, an interference fit between the retainer-pin 219 and the hollow retainer-pin 228 firmly secures the handle housing 220 and the handle base 210 together. The limit ribs 226 limit the axial displacement of the rotary-shaft 238, but the rotary-shaft 238 is allowed to rotate around its own axis.

Figure 8:
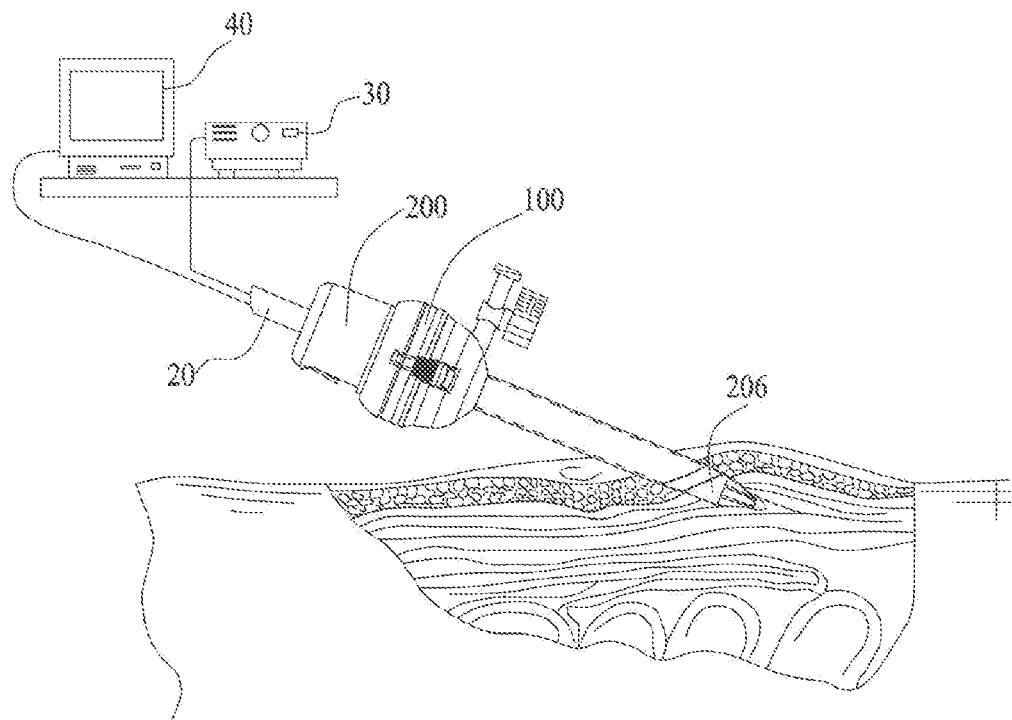
FIG. 8 is a simulated view of trocar in FIG. 1 in the clinical application.

Referring to FIGS. 5, 7 and 8, the function of the cam lock 230 is disclosed. Referring to FIGS. 7 and 8, when the endoscope 20 is inserted, the cam lock 230 is rotated transversely and inward around the rotary-shaft 238 until the cam lip 236 is contacted with the endoscope 20, and continue to rotate so that the cantilever 218 are forced to deform, thereby causing mutual compression between the cam lip 236 and the endoscope 20, and restricting the axial displacement of the endoscope 20. Referring to FIG. 5, when the cam lock 230 is rotated transversely outward around the rotary-shaft 238 until the cam lip 236 is separated from the endoscope 20, the endoscope 20 can be easily inserted and removed. Various endoscope lock mechanisms is disclosed in U.S. Pat. Nos. 5,569,291, 7,823,327, 8,608,769. Those skilled in the art will appreciate that adaptable modifications of the above inventions can be used in the present invention, and other endoscope lock mechanisms are also conceivable.

Referring to FIGS. 6 and 7, the elongate shaft 240 includes the axis aperture 242. In the present embodiment, the hollow shaft 240 is made of a metal material that is connected with the elongated shaft 214 of the handle base 210. There are various ways to secure the hollow shaft 240 and the handle base 210, wherein glue bonding and embedded injection are the two most common methods. While the hollow shaft 240 can also be made of a plastic material, and the hollow shaft 240 and the handle base 210 can be injection molded into a single component. The transparent tip 250 is made of a transparent plastic, including but not limited to transparent PC, transparent PMMA, transparent PP, transparent PET, transparent PS, COC, Tritan of Eastman Chemical, transparent ABS, and so on.

Figure 9:
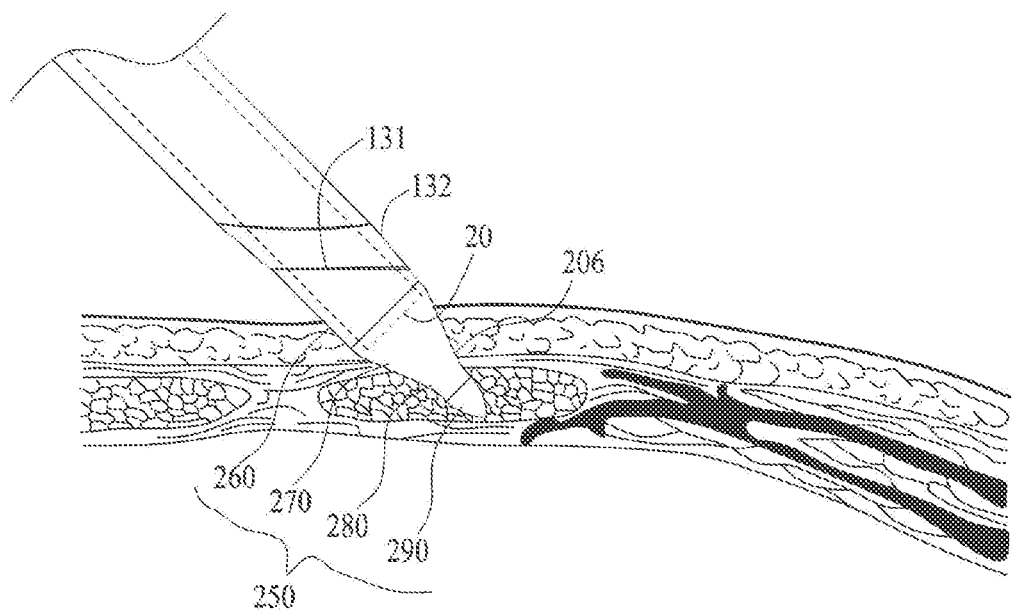
FIG. 9 is a simulated view of distal-end portion in FIG. 1 in the clinical application.
Figure 10:
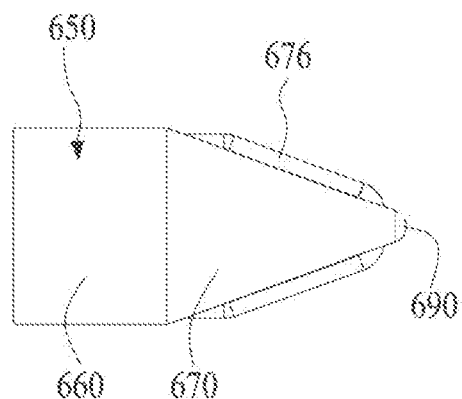
FIG. 10 is a side projection view of the transparent tip 650 in the prior art.
Figure 11:
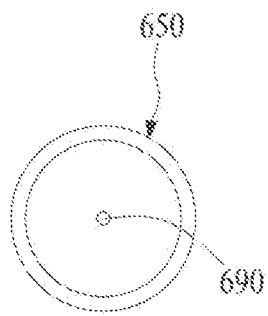
FIG. 11 is a projection view of the transparent tip from the proximal end to the distal end in FIG. 10.

Referring to FIGS. 8 and 9, the obturator 200 through the cannula 100 forms a trocar 1000, and the surgeon operates the trocar 1000 to access into the body cavity through a incision ceared at the patient penetrating site. Optionally, a matched endoscope 20 (i.e. 10 mm, 5 mm diameter rigid endoscopes or soft lens) can be inserted into the obturator 200; the light source 30 provides light via endoscope 20 to illuminate distal-end portion 206 of the obturator 200; and the light reflected by the muscle and tissue wrapped outside the distal-end portion 206 is received by the endoscope and transmitted to the imaging and display device 40. Therefore, during the penetrating process or during the gradual deepening of the distal-end portion 206 in the patient's muscle and tissue, the surgeon can observe the actual working condition of the distal-end portion 206 through the imaging and display device 40 so that the surgeon can control the entire penetrating process. Particularly, the surgeon can observe real-time the insertion depth of the most distal apex of the obturator 200 into the body cavity of the patient, the specific position and the tissue image attached to the surface of the patient through a camera and a display device to inhibit damage to interior organs, such as an accident, such as accidentally stabbing the liver, accidentally piercing the large intestine, etc.

Figure 12:
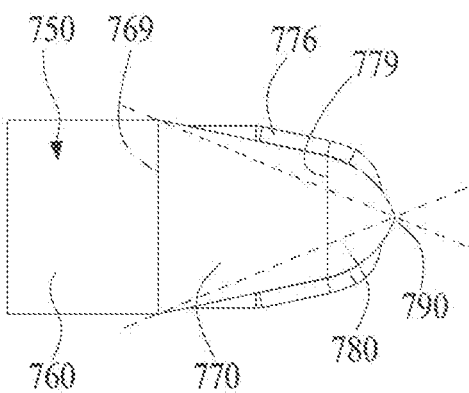
FIG. 12 is a side projection view of the transparent tip 750 in the prior art.
Figure 13:
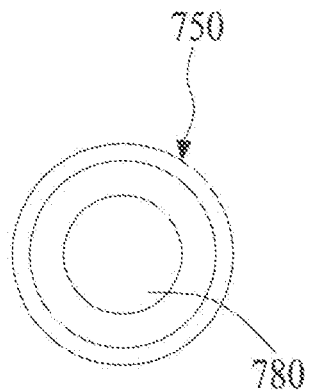
FIG. 13 is a projection view of the transparent tip from the proximal end to the distal end in FIG. 12.
Figure 14:
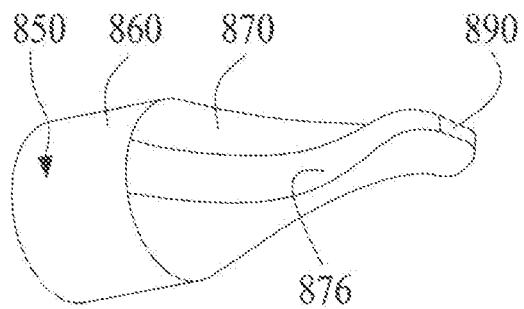
FIG. 14 is a 3D perspective view of the transparent tip 850 in the prior art.

As described in the background, the penetration force is large when using the bladeless obturator. Those skilled in the art should understand that when using a transparent bladeless obturator not only is the penetration force large, but also the operation is difficult (because of the endoscope, fiber-optical cable and video cable). Since the first the transparent bladeless obturator has been introduced, improved researches on visual bladeless penetration have never stopped. FIG. 10-19 show the structure of the distal-end portion of four transparent bladeless obturators that are currently commercialized and most commonly used in clinical applications. FIG. 10-19 describe the earliest commercially transparent obturator 600 (not shown) that includes a transparent conical tip 650. The transparent tip 650 includes a hollow cylinder 660 and a top end 690 with a hollow cone 670 there between, which comprising two approximately symmetric edges 676. FIG. 12-13 describe a modified transparent obturator 700 (not shown) based on said obturator 600, the transparent obturator 700 including a modified conical transparent tip 750. The transparent tip includes a hollow cylinder 760 and a top-end 790, one end of the hollow cone 770 intersects the hollow cylinder 760 to form a line 769, the other end of which extends toward the distal end and intersects the hollow hemisphere 780 at a line 779, and the hollow hemisphere 780 extends toward the distal end to the top end 790, the hollow cylinder 760 comprising two approximately symmetric edges 776 Through the top end 790 and the intersection line 769 as a virtual conical surface, it can be seen that the obturator 700 has a locally convex and approximately hollow hemisphere 780 adjacent the region of the top end 790 opposite to the obturator 600. Those skilled in the art should appreciate that under the same condition of the endoscope, camera and display device, the hollow hemisphere 780 allows the obturator 700 to obtain a sharper pattern and a wider field of view of the top end 790 and its adjacent region. Studies have shown that clinicians tend to focus on visual effects, so that the obturator 600 have been substantially completely replaced by the obturator 700 in the current commercial and clinical application. However, the obturator 700 still has shortcomings, a 12 mm diameter obturator with the structure similar to the obturator 700 is disclosed in the application US20070066988. The penetration force of the obturator is about 15 pounds. Such a large penetration force increases the control difficulty of the operation that it increases the risk of damage to interior organs. The application US20070066988 has been discussed theoretically for reducing the penetration force, but unfortunately, a valid substantial solution has not been proposed, so the application has been rejected.

Figure 15:
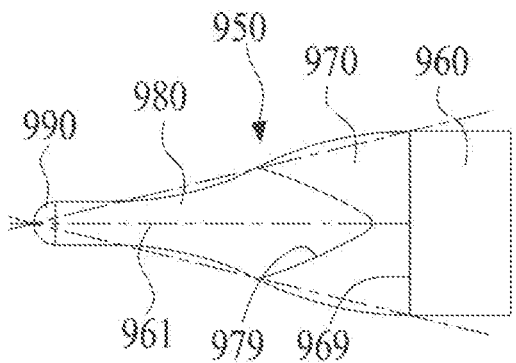
FIG. 15 is a side projection view of the transparent tip 950 in the prior art.
Figure 16:
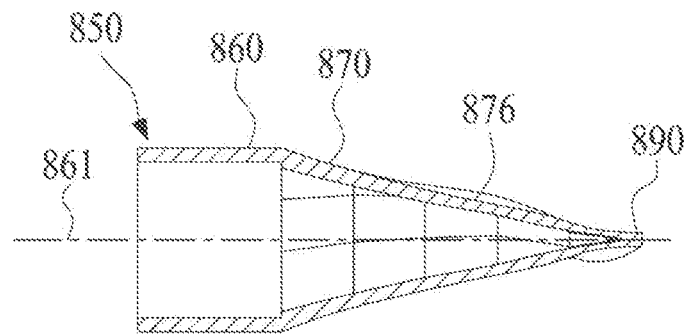
FIG. 16: shows a longitudinal-section view of the transparent tip in FIG. 14.
Figure 17:
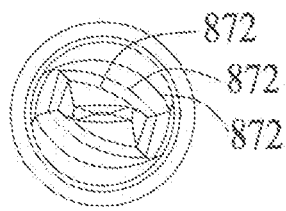
FIG. 17 is a projection view of the transparent tip from the proximal end to the distal end in FIG. 14.
Figure 18:
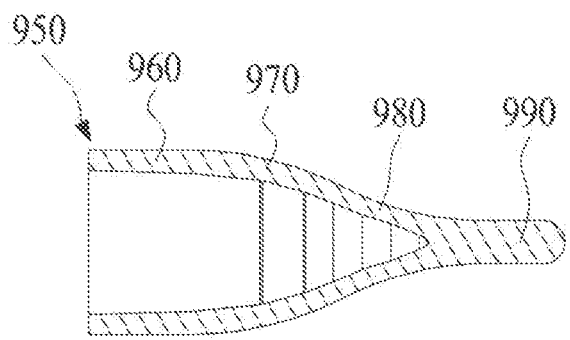
FIG. 18: shows a longitudinal-section view of the transparent tip in FIG. 15.
Figure 19:
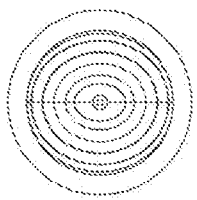
FIG. 19 is a projection view of the transparent tip from the proximal end to the distal end in FIG. 15.
Figure 20:
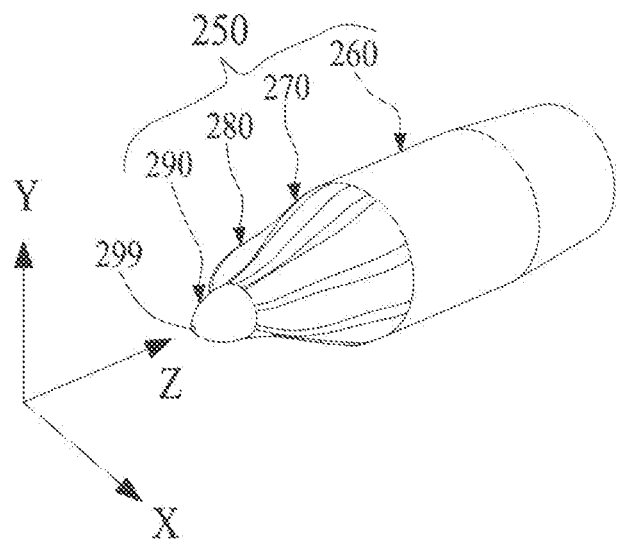
FIG. 20 is a 3D perspective view of the transparent tip in FIG. 3.

Referring to 14, FIGS. 16 and 17 show another improved transparent obturator 800 (not shown). The transparent obturator 800 includes a transparent drill-shape tip 850. The tip 850 includes a proximal hollow cylinder 860 and a top end 890 with a beveled-portion 870 there between. The hollow cylinder 860 includes an axis 861. The top end 890 is an approximately rectangular narrow blade-shape structure, the beveled-portion 870 is continuously swept from the distal end to the proximal end along the axis 861 by the approximately rectangular section 872, and during the sweeping process, the length and width of the rectangular section 872 gradually increase and gradually twist to form two spiral drill-edges 876. FIGS. 15, 18 and 19 illustrate another improved transparent obturator 900 (not shown). The transparent obturator 900 has a transparent oval tip 950. The tip 950 includes an axis 961, a hollow cylinder 960 and a papillary tip 990. The hollow cylinder 960 at one end of the expand-portion 970 intersects to form a line 969, the other end of which extends toward the distal end and intersects the import-portion 980 at the line 979. Through the top end 990 and the intersection line 969 drawing a virtual conical curved-surface, wherein the import-portion 980 includes a concave curved-surface, while the expand-portion 970 includes a gradually convex curved-surface, and the cross-section of the import-portion 980 and the expand-portion 970 perpendicular to the axis 961 is oval. The transparent tips 850 and 950 respectively propose effective measures for reducing the penetration force from different perspectives. However, when the penetration force is reduced, it greatly has a bad effect to the visual. Referring to FIGS. 9, 17 and 19, when the transparent tip 850 or the transparent tip 950 penetrates into the patient's muscle and tissue, the imaging of the muscle and tissue wrapped outside the transparent tip is twisted, which has a bad effect to the visual. In addition, referring to FIGS. 16 and 18, the material of the transparent tip 850, which is formed at the top end 890, inevitably abruptly thickens, thereby affecting the sharpness of the partial imaging of the top end 890. Likewise, the transparent tip 950 inevitably creates a sudden thickening of the material at the top end 990, thereby affecting the partial imaging sharpness of the top end 990.

Studies have shown that most surgeons tend to sacrifice operational convenience for clearer image and are less willing to sacrifice visual effect to reduce penetration. That is to say, most surgeons are more willing to trust their eyes than to trust their own hands. This is the difference of the transparent bladeless obturator from the other bladeless obturator and a blade-protective obturator. So far, there have been no perfect balance of the visual effect and the penetration force in the disclosed and commercialized transparent bladeless obturators. To obtain a more perfect effect, or simply to find a better solution, you must start with the surgeon's most important needs and solve the problem from a more detailed perspective. So far, in the disclosed technology, the designer usually considers the visual effect of the transparent tip, but ignoring the real needs of the surgeon. Those skilled in the art could appreciate that the transparent bladeless obturator and the using method thereof, the most fundamental and core function is to inhibit damage to interior organs during the penetration. Those skilled in the art of clinical penetration operations could appreciate that the apex of the obturator and its adjacent region are liable to damage the internal organs of the patient, and the other parts of the puncture needle have a low probability of damaging the internal organs of the patient. Therefore, a better solution to balance the visual effect and the penetration force should ensure that the visual effect of the top-end of the transparent tip and its adjacent region is protected or improved when measures to reduce the penetration force are used; if necessary, sacrifice the visual effect outside its adjacent region.

FIGS. 20-23 describe the transparent tip 250 in more detail. The transparent tip 250 is divided into 4 portions, from the distal end to the proximal end, a top-portion 290, a spear-portion 280, a transition-portion 270 and a base-portion 260. The transparent tip 250 includes a longitudinal axis (labeled as Z-direction), the first transverse direction (labeled as X-direction) and the second transverse direction (labeled as Y-direction), wherein the X-direction, the Y-direction, and the Z-direction are substantially perpendicular to each other.

Figure 21:
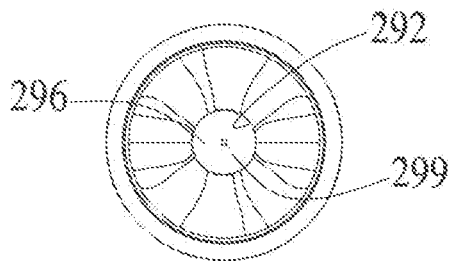
FIG. 21 is a projection view of the transparent tip from the proximal end to the distal end in FIG. 20.
Figure 22:
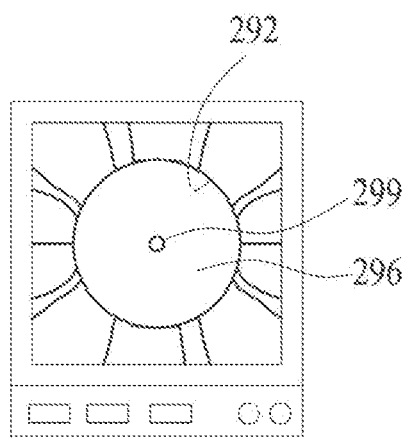
FIG. 22 is a partial-enlarged-simulated view of the transparent tip of FIG. 20 in the clinical application.
Figure 23:
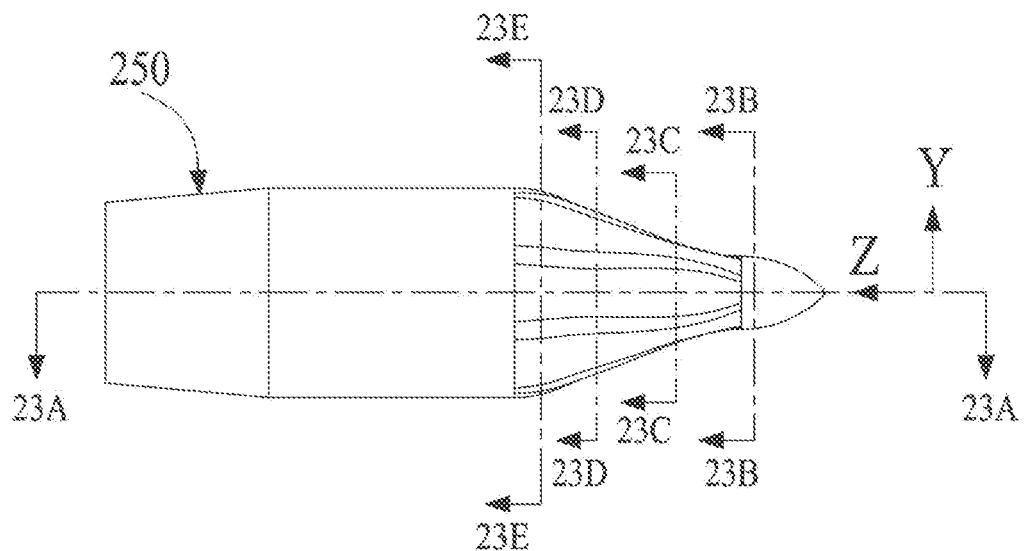
FIG. 23 is a side projection view of the transparent tip in FIG. 20.
Figure 23A:
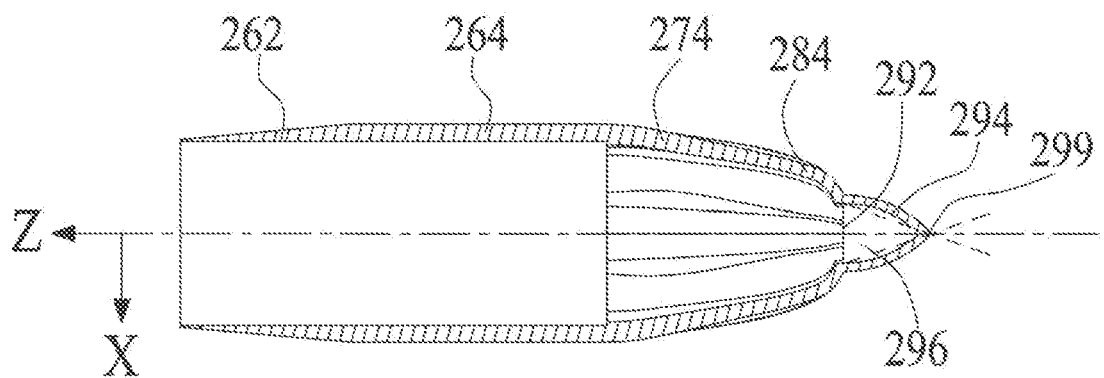
FIG. 23A is a cross-section view taken along line 23A-23A of FIG. 23.
Figure 23B:
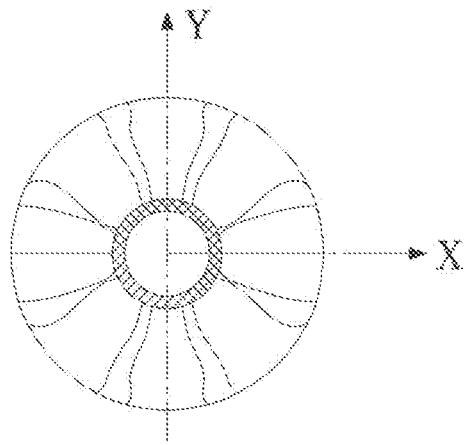
FIG. 23B is a cross-section view taken along line 23B-23B of FIG. 23.

Referring to FIG. 7, FIGS. 20-23, FIGS. 23A and 23B, the top-portion 290 includes an apex 299, a rotary-wall 294 which extends from the apex 299 toward the proximal end and gradually increases, said rotary-wall 294 shaping the hollow cone 296, said rotary-wall 294 and said spear-portion 280 extending to be intersected and form a circular field of vision 292. Referring to FIG. 23A, optionally, the rotary-wall 294 has a convex-shape, i.e., through the apex 299 and the circular field of vision 292 drawing a conical surface, the rotary-wall 294 is outside the conical surface. FIG. 21 is a projection view of the transparent tip 250 from the proximal end to the distal end. Combined with the foregoing, those skilled in the art of clinical penetration operations could appreciate that the surgeon normally does not care about the image quality within the entire projected view, but rather desire the apex 299 and its adjacent region (i.e. the inner region limited by the circular field of vision 292 in this embodiment) are sufficiently clear, which allows the surgeon have a real-time observation of the depth at which the apex of the obturator and its adjacent region penetrate the body cavity of the patient and the true state of the attached muscle or tissue. Therefore, the circular field of vision 292 is limited in the region, and the rotary-wall 294 should be axisymmetric and uniform in the thickness to reduce image differences (distortion) caused by optical differences by the structure of the rotating wall 294 itself. Those skilled in the art of clinical penetration operations could appreciate that almost all of the camera and display device 40 in the clinical application have functions of digital zoom and partial zoom. While the closer the object is to the endoscope, the clearer the image is. The circular field of vision 292 of the invention further has the function of guiding the surgeon to focus and adjust the display screen. Referring to FIGS. 21-22, optionally, the region outside the circular field of vision 292 contains a distorted or uneven geometry that makes the image outside the circular field to be less clear, and guiding the surgeon to focus or magnify the image with the inner region of the circular field of vision 292 as a target.

Referring to FIGS. 6-7, FIGS. 23 and 23A, the spear-portion 280 includes a sweeping-wall 284 that is connected with the rotary-wall 294. The sweeping-wall 284 extends from the distal end to the proximal end along the Z-direction and gradually increases in size of the X-direction and the Y-direction. The transition-portion 270 includes a sweeping-wall 274 that is connected to the sweeping-wall 284 with smooth transition, that is, there is no obvious boundary between the sweeping-wall 274 and the sweeping-wall 284. The sweeping-wall 274 extends from the distal end to the proximal end along the Z-direction and gradually increases in size of the X-direction and the Y-direction. The base-portion 260 includes a proximal beveled-wall 262 and a distal cylindrical-wall 264 that is connected to the sweeping-wall 274 with smooth transition.

Figure 23C:
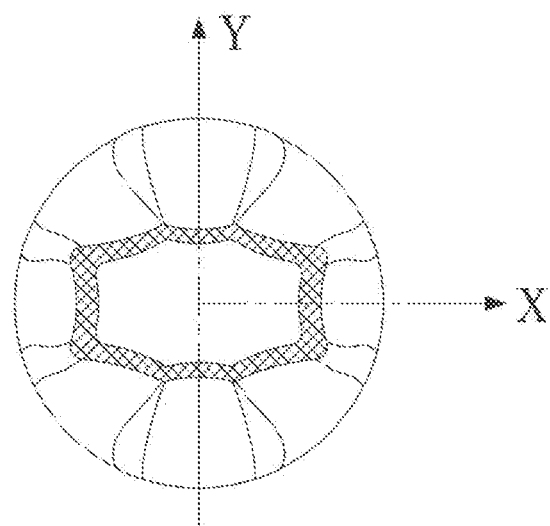
FIG. 23C is a cross-section view taken along line 23C-23C of FIG. 23.
Figure 23D:
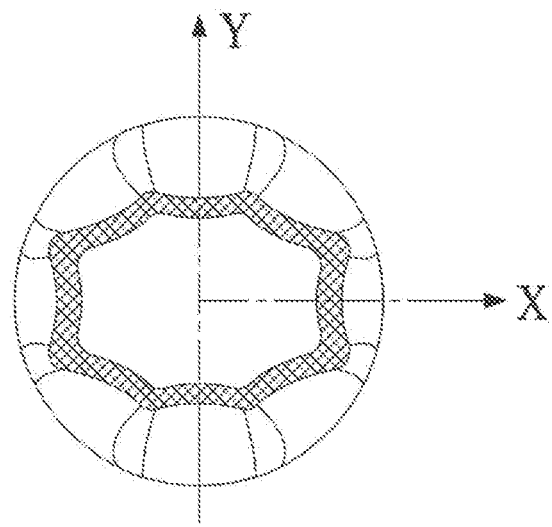
FIG. 23D is a cross-section view taken along line 23D-23D of FIG. 23.

Referring to FIGS. 6 and 23A, FIGS. 7 and 23, combined with FIG. 23C and FIG. 23D. The spear-portion 280 includes the first transverse portion (X-direction) and the second transverse portion (Y-direction), and the dimension of the first transverse portion is greater than the dimension of the second transverse portion. The transverse dimension is obtained at the widest (or longest) portion of the transverse portion measured in any cross section substantially perpendicular to the longitudinal axis, and the raised blade structure should be ignored during measurement (as shown in FIGS. 30C and 30D). From the distal end to the proximal end, the dimensions of the first transverse portion (X-direction) and the second transverse portion (Y-direction) of the spear-portion 280 are simultaneously increased, and from the distal end to the proximal end the dimension ratio of the X-direction/Y-direction is getting smaller and smaller. For example, the dimension ratio of the X-direction/Y-direction in FIG. 23D is smaller than which of the X-direction/Y-direction in FIG. 23C.

Figure 23E:
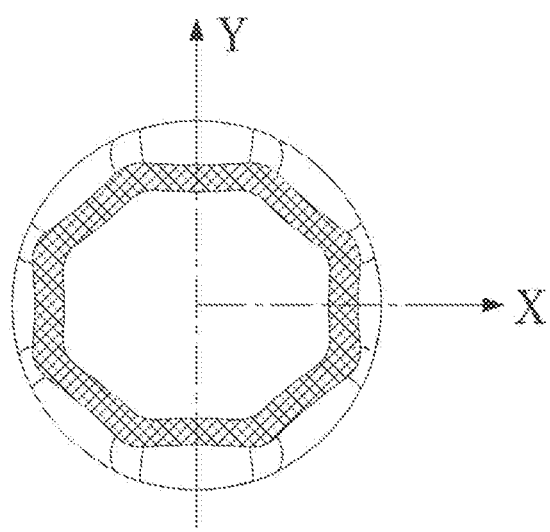
FIG. 23E is a cross-section view taken along line 23E-23E of FIG. 23.

Referring to FIGS. 6 and 23A, FIGS. 7 and 23, in combination with FIG. 23D and FIG. 23E. The partial portion which the transition-portion 270 is connected to the spear-portion 280 has a dimension in the X-direction that is larger than the dimension in the Y-direction. From the distal end to the proximal end, the dimensions of X-direction and Y-direction of transition-portion 270 are simultaneously increased, and from the distal end to the proximal end the dimension ratio of the X-direction/Y-direction is getting smaller and smaller, until Y-dimension is equal to X-dimension. For example, the X-dimension in FIG. 23D is larger than the Y-dimension, and the X-dimension i and Y-dimension in FIG. 23E are substantially equal. In the present embodiment, the cross-sectional geometry disclosed in FIGS. 23C, 23D, and 23E is 8-sided shape, but may be oval or other shapes.

In the transparent tip 250 of the present invention, the top-portion 290 ensures that the obturator 200 has a good visual effect. While the spear-portion 280 makes the overall transparent tip 250 as approximately spear-shaped. When the top-portion 290 is inserted into the patient's muscle, the spear-portion 280 reduces the penetrated volume, thereby facilitating reducing the resistance to penetration. When the patient is penetrated in a manner of rotating back and forth, the spear-portion facilitates tearing the muscle, thereby reducing the resistance of the torn tissue and the expansion force of the subsequent inflated wound. Optionally, the geometric relationship of the circular field of vision 292, herein conforms to the following equation:

$$2 \text{ mm} \leq D \leq 0.5 D_0.$$

wherein:

D=diameter of the circular field of vision 292;

$D_0$=the maximum outer diameter of the distal-end portion 206 of the obturator.

Those skilled in the art will understand that when the diameter of the circular field of vision 292 is less than 2 mm, the hollow cone 296 is difficult to manufacture and the circular field of vision 292 is too small in the display image. When the diameter of the circular field of view 292 is greater than 0.5 D0, the penetration force is large or the improvement in the penetration force relative to the prior art is not significant.

Figure 24:
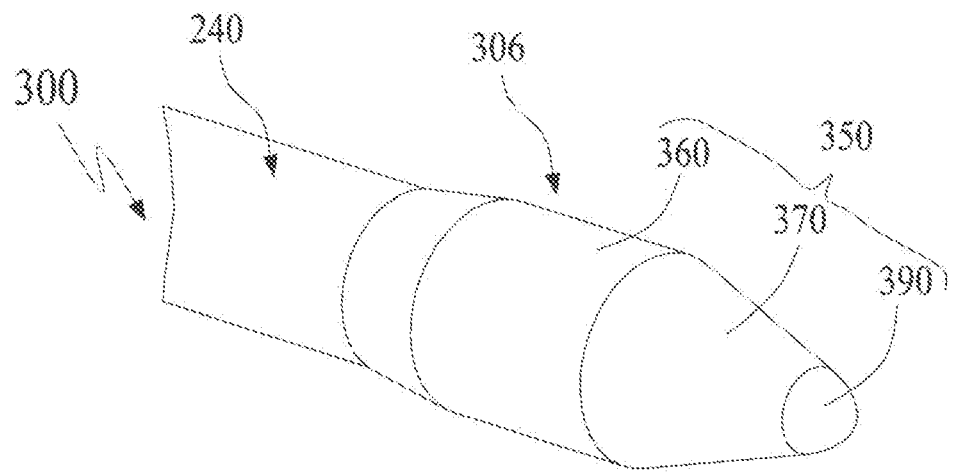
FIG. 24 is a 3D perspective view of the distal-end portion in the second embodiment of the invention.
Figure 25:
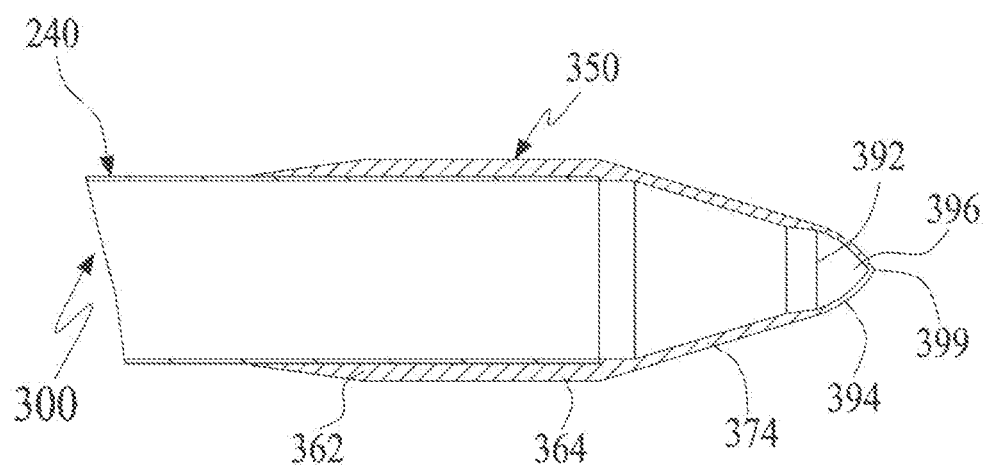
FIG. 25: shows a longitudinal-section view of the distal-end portion in FIG. 24.
Figure 26:
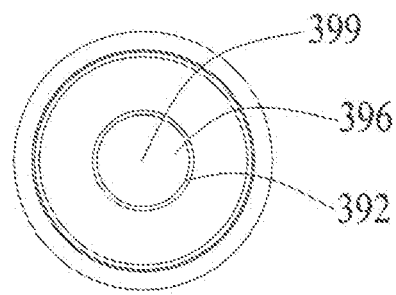
FIG. 26 is a projection view of the distal-end portion from the proximal end to the distal end in FIG. 24.

FIG. 24-26 show detailed depiction of the transparent bladeless obturator 300 in the second embodiment of the invention. The transparent bladeless obturator 300 is composed of a handle 202, a shaft 204 and the distal-end portion 306. The transparent bladeless obturator 300 includes a handle 202 and a shaft 204 that are identical to the obturator 200, so no more tautology herein. Said distal-end portion 306 includes a transparent tip 350.

FIGS. 24-26, the transparent tip 350 is divided into 3 portions, from the distal end to the proximal end, a top-portion 390, a main-portion 370 and a base-portion 360. The top-portion 390 includes an apex 399, a rotary-wall 394 which extends from the apex 399 toward the proximal end and gradually increases, said rotary-wall 394 limiting the hollow cone 396, said rotary-wall 394 and said main-portion 370 extending to be intersected and form a circular field of vision 392. Referring to FIG. 25, optionally, the rotary-wall 394 has a convex-shape, i.e., through the apex 399 and the circular field of vision 392 drawing a conical surface, the rotary-wall 394 is outside the conical surface. The main-portion 370 includes a main-body wall 374, the main-body wall 374 is connected with the rotary-wall 394. The main-body wall extends axially from the distal end toward the proximal end and gradually increases in a transverse dimension. The base-portion 360 includes a proximal beveled-wall 362 and a distal cylindrical-wall 364, which is connected to the sweeping-wall 284 with smooth transition.

In an optional embodiment, the thickness of the inner region limited by the circular field of vision 392 is thinner than the thickness of the outer region of the circular field of vision 392. That is, the thickness of the rotary-wall 394 in the second embodiment is thinner than the thickness of the main-body wall 374. In a preferred embodiment, the thickness of the rotary-wall 394 is 0.25 to 0.45 mm, and the thickness of the main-body wall 374 is 0.5 to 0.75 mm.

It will be readily understood by one of the ordinary skilled in the art that, from the perspective of manufacturing, it is a poor design (it is very easy to cause manufacturing defects) that the thickness of the inner region of the circular field of vision in the present embodiment is thinner than the thickness of the outer region. So far, the transparent tip 350 can only be produced by injection molding, and the injection port can only be designed on the base-portion 360. Under the normal production condition, the thickness at the rotary-wall 394 and the apex 399 should be much thicker than the thickness of the main-body wall 374, otherwise the apex 399 and its adjacent region are difficult to be filled or severely shrunk. The transparent obturator is disclosed in the 10th to 25th lines in the fifth page of U.S. Pat. No. 8,506,520, that the overall uniform thickness of the transparent tip is favorable for obtaining clear images, while the transparent tip with uneven thickness cannot obtain clear images. The structure is disclosed in FIG. 1C, FIG. 1D, FIG. 2A and FIG. 2B of U.S. Pat. No. 8,506,520, although the transparent tip has an overall uniform thickness, the thickness of the apex (top) of the transparent tip and its adjacent region is significantly thicker than the other parts. Coincidentally, the transparent obturator is disclosed in the application US20150216560 and US20150313631, wherein the transparent tip has an overall uniform thickness, the thickness of the apex (top) of the transparent tip and its adjacent region is significantly thicker than the other parts. Studies have shown that, so for, the transparent tip of the disclosed and commercialized transparent obturator are adopted an uniform thickness or a thicker structure at the top of the transparent tip.

U.S. Pat. No. 8,506,520 discloses that the uniform thickness of the transparent facilitates obtaining a clear overall image. While those skilled in the art of clinical penetration operations could appreciate that the surgeon normally does not care about the image quality within the entire projected view, but rather desire the apex and its adjacent region (i.e. the inner region defined by the circular field of vision 392 in this embodiment) are sufficiently clear, which allows the surgeon have a real-time observation of the depth at which the apex of the obturator and its adjacent region penetrate the body cavity of the patient and the true state of the attached muscle or tissue. Therefore, the circular field of vision 392 is defined in the region, and the rotary-wall 394 should be axisymmetric and uniform in the thickness to reduce image differences (distortion) caused by optical differences by the structure of the rotating wall 394 itself. Those skilled in the art could understand that the light transmittance of any transparent material is less than 100%, so reducing the thickness of the transparent tip is advantageous for reducing light loss and obtaining a clearer image. In the present embodiment, the area inside the circular field of vision 392, adopting a thinner thickness (e.g., 0.25-0.45 mm), facilitates sharper images within the circular field of vision 392. Meanwhile, the size span of the area inside the circular field of vision 392 is small and the thinner thickness still has sufficient structural strength. Whereas the area outside the circular field of vision 392 is thicker (e.g., 0.5 to 0.75 mm). The size span of the area gradually increase and the thicker thickness can obtain sufficient structural strength. Those skilled in the art of clinical penetration operations could appreciate that that almost all of the camera and display device 40 in the clinical application have functions of digital zoom and partial zoom. The thickness inside the circular field of vision 392 is significantly less than the thickness outside the circular field of vision 392, which makes the image inside the circular field of vision 392 clearer, thereby guiding the surgeon to focus or partially enlarge the image with the inner region of the circular field of vision 392 as a target.

The transparent tip 350 is more difficult to manufacture than the transparent tip disclosed in the prior art. However, it can be optimized from the aspects of material selection, structure and injection molding process to reduce the manufacturing difficulty. Studies have shown that the use of high-flow transparent materials can help reduce the negative rate of the transparent tip, such as Eastman's high-flow Tritan, high-flow COC, or high-flow PC. In the prior art, it is usually manufactured by two moldings: integral molding (that is, the hollow shaft and the transparent tip are molding from the same material) or overmolding (i.e., the metal hollow tube embedded molding) to improve production effectiveness. However, the two manufacturing methods are prone to large errors in the thickness of the top end of the transparent tip, which in the present example is relatively thin, and it is easy to cause defective products by integral molding or overmolding. The transparent tip can be separately molded and manufactured by bonding with the hollow shaft, for example, by UV glue to cure the production efficiency can still be improved. In the injection molding process, adopting hot runner, enlarging the nozzle, reducing the mold temperature, reducing the injection pressure, increasing the holding-pressure time and other methods for injection molding can reduce the defect rate. It must be noted that the problem of molding dissatisfaction is usually solved by increasing the mold temperature and increasing the molding pressure, but it is not applicable to this embodiment. Increasing the mold temperature tends to cause the transparent material yellowing, thereby affecting the image effect; while increasing the molding pressure tends to cause stress concentration, thereby the transparent tip to be cracked (the tendency is obvious when the transparent tip adopts PC material).

Although in the transparent tip described in this embodiment, due to the thinner thickness of the top-portion the production difficulty and the production are increased, it can provide a better experience for clinical applications, which sacrifice is worthwhile, and which production difficulty can be reduced by a series of improvement measures.

FIG. 27-30 show detailed depiction of the transparent bladeless obturator 400 in the third embodiment of the invention. The transparent bladeless obturator 400 is composed of a handle 202, a shaft 204 and the distal-end portion 406. The transparent bladeless obturator 400 includes a handle 202 and a shaft 204 that are identical to the obturator 200, which are not described herein. Said distal-end portion 406 includes a transparent tip 450.

Figure 27:
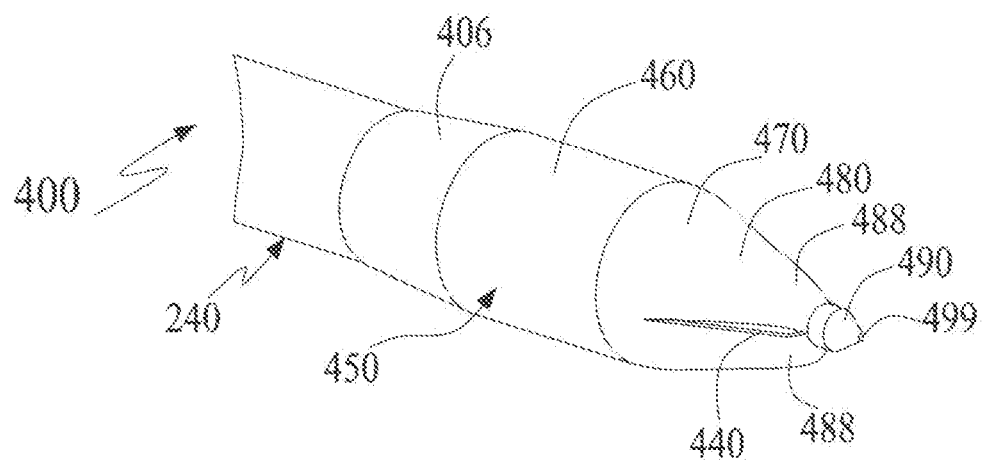
FIG. 27 is a 3D perspective view of the distal-end portion in the third embodiment of the invention.

Referring to FIG. 27, the transparent tip 450 is divided into 4 portions, from the distal end to the proximal end, a top-portion 490, a spear-portion 480, a transition-portion 470 and a base-portion 460. The transparent tip 450 includes a longitudinal axis (labeled as K-direction), the first transverse direction (labeled as M-direction) and the second transverse direction (labeled as N-direction), wherein the M-direction, the N-direction, and the K-direction are substantially perpendicular to each other.

Figure 28:
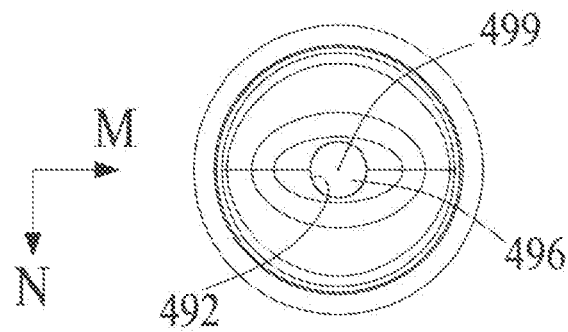
FIG. 28 is a projection view of the distal-end portion from the proximal end to the distal end in FIG. 27.
Figure 29:
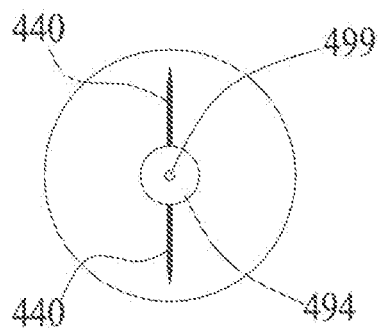
FIG. 29 is a projection view of the distal-end portion from the proximal end to the distal end in FIG. 27.
Figure 30:
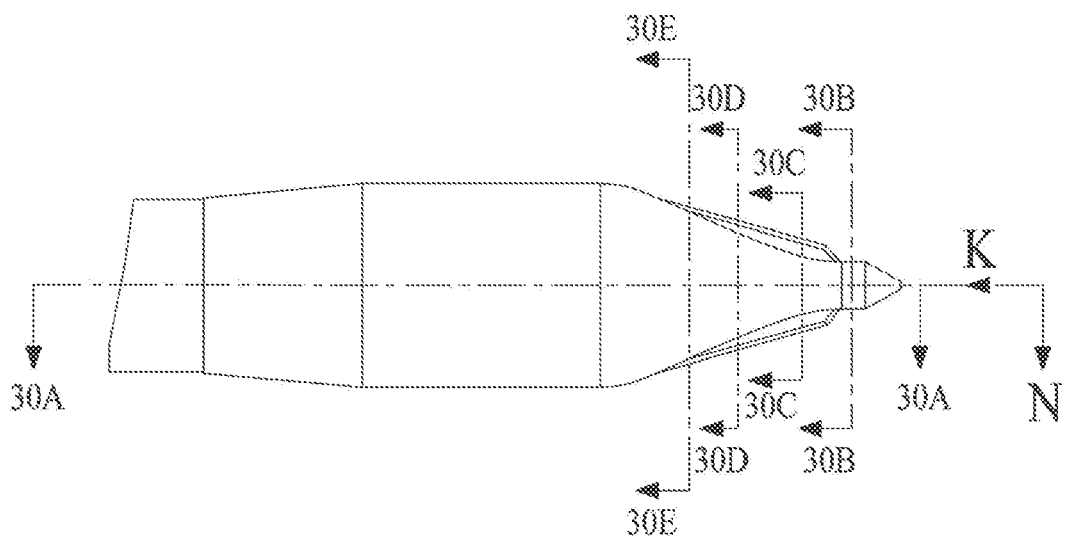
FIG. 30 is a side projection view of the distal-end portion in FIG. 27.
Figure 30A:
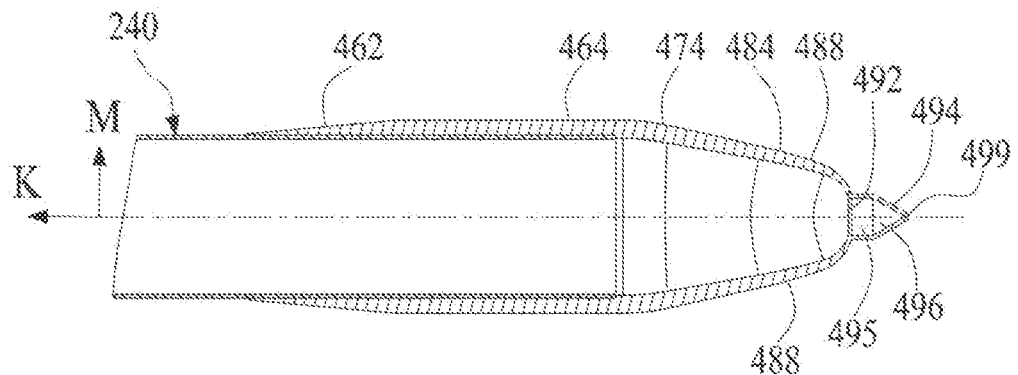
FIG. 30A is a cross-section view taken along line 30A-30A of FIG. 30.
Figure 30B:
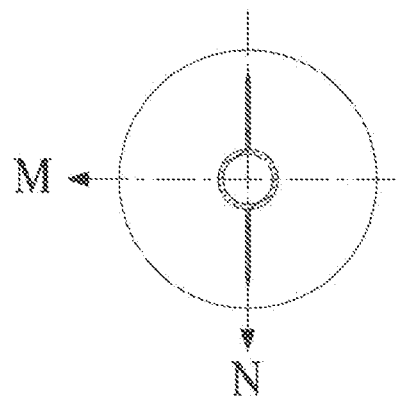
FIG. 30B is a cross-section view taken along line 30B-30B of FIG. 30.
Figure 30C:
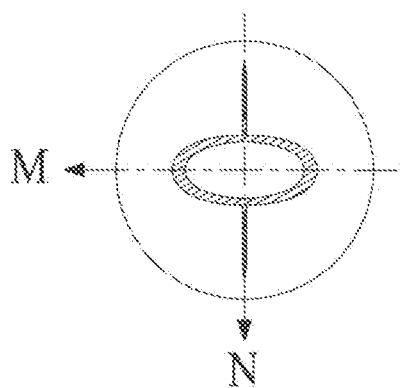
FIG. 30C is a cross-section view taken along line 30C-30C of FIG. 30.
Figure 30D:
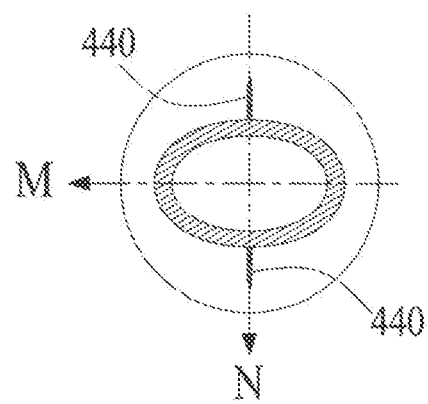
FIG. 30D is a cross-section view taken along line 30D-30D of FIG. 30.

Referring to FIGS. 27-30, FIGS. 30A and 30B, mainly FIG. 30A. The top-portion 490 includes an apex 499, a rotary-wall 494 which extends from the apex 499 toward the proximal end and gradually increases. Said rotary-wall 494 comprises two portions, a conical wall and a cylindrical wall, but it is also possible to include only a rotary-wall with an approximately conical-shape. Said rotary-wall 494 limits the hollow cone 496 and said the hollow cylinder 495. The rotary-wall 494 and said spear-portion 480 extending to be intersected and form a circular field of vision 492. FIG. 28 is a projection view of the transparent tip 450 from the proximal end to the distal end. Combined with the foregoing, those skilled in the art of clinical penetration operations could appreciate that the surgeon normally does not care about the image quality within the entire projected view, but rather desire the apex 499 and its adjacent region (i.e. the inner region limited by the circular field of vision 492 in this embodiment) are sufficiently clear, which allows the surgeon have a real-time observation of the depth at which the apex of the obturator and its adjacent region penetrate the body cavity of the patient and the true state of the attached muscle or tissue. Therefore, the circular field of vision 492 is defined in the region, and the rotary-wall 494 should be axisymmetric and uniform in the thickness to reduce image differences (distortion) caused by optical differences by the structure of the rotating wall 494 itself. Those skilled in the art of clinical penetration operations could appreciate that almost all of the camera and display device 40 in the clinical application have functions of digital zoom and partial zoom, while the closer the object is to the endoscope, the clearer the image is. The circular field of vision 492 in the present invention can also guide the surgeon to focus or partially magnify the image with the inner region of the circular field of vision 292 as a target.

Referring to FIG. 30 and FIG. 30A, in combination with FIG. 30C and FIG. 30D. The spear-portion 480 includes the first transverse portion (M-direction) and the second transverse portion (N-direction), and the dimension of the first transverse portion is greater than the dimension of the second transverse portion. Therefore, the first transverse portion is also referred to as a wide-thick direction, and the second transverse portion is referred to as a narrow-thin direction. From the distal end to the proximal end, the dimensions of M-direction and N-direction of the spear-portion 480 are simultaneously increased, and from the distal end to the proximal end the dimension ratio of the M-direction/N-direction is getting smaller and smaller. For example, the dimension ratio of the X-direction/Y-direction in FIG. 30D is smaller than which of the X-direction/Y-direction in FIG. 30C. The first transverse portion of the spear-portion 480 extends transversely from the center to the sides to form two substantially symmetrical and atraumatic blunt separating-portions 488.

Referring to FIGS. 27-30 and FIGS. 30A and 30B, mainly FIG. 30A. The spear-portion 480 includes a sweeping-wall 484 that is connected with the rotary-wall 494. The sweeping-wall 484 extends from the distal end to the proximal end along the K-direction and gradually increases in size of the M-direction and the N-direction. The transition-portion 470 includes a sweeping-wall 474 that is connected to the sweeping-wall 484 with smooth transition, that is, there is no obvious boundary between the sweeping-wall 474 and the sweeping-wall 484. The sweeping-wall 474 extends from the distal end to the proximal end along the K-direction and gradually increases in size of the M-direction and the N-direction. The base-portion 460 includes a proximal beveled-wall 462 and a distal cylindrical-wall 464 that is connected to the sweeping-wall 284 with smooth transition.

Figure 30E:
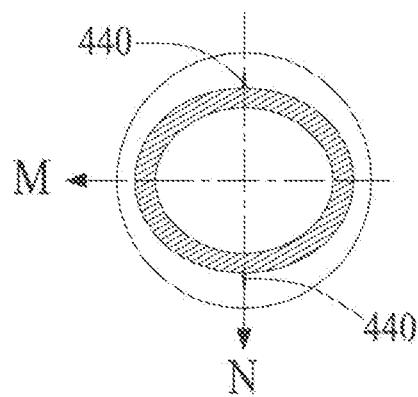
FIG. 30E is a cross-section view taken along line 30E-30E of FIG. 30.

Referring to FIG. 30 and FIG. 30A, in combination with FIG. 30D and FIG. 30E. The partial portion which the transition-portion 470 is connected to the spear-portion 480 has a dimension in the M-direction that is larger than the dimension in the N-direction. From the distal end to the proximal end, the dimensions of M-direction and N-direction of transition-portion 470 are simultaneously increased, and from the distal end to the proximal end the dimension ratio of the M-direction/N-direction is getting smaller and smaller, until N-dimension is equal to M-dimension. For example, the M-dimension in FIG. 30D is larger than the N-dimension, and the M-dimension i and N-dimension in FIG. 30E are substantially equal. In the present embodiment, the cross-sectional geometry disclosed in FIGS. 23C, 23D, and 23E is oval, but may be polygonal or other shapes.

In the transparent tip 450 of the present invention, the top-portion 490 ensures that the obturator 400 has a good visual effect. While the spear-portion 480 makes the overall transparent tip 450 as approximately spear-shaped. When the top-portion 490 is inserted into the patient's muscle, the spear-portion 480 reduces the penetrated volume, thereby facilitating reducing the resistance to penetration.

Referring to FIG. 27-30, the transparent tip 450 further includes at least one blade-shaped working-edge 440. In the present embodiment, there are two substantially symmetrical working edges 440. In the transverse direction, the working-edge 440 extends outwardly from the outer surface of the sweeping-wall 484 and the sweeping-wall 474 and from the middle of the outer surface of the narrow-thin side (i.e., N-direction) of the transparent tip 450 extends outward along the second transverse portion (N-direction) The working-edge 440 is substantially perpendicular to the first transverse portion. In the longitudinal axis direction (K-direction), the working-edge 440 extends from the outer surface of the spear-portion 480 to the outer surface of the transition portion 470. In a preferred embodiment, the working-edge 440 is outside the area limited by the circular field of vision 492 to avoid affecting the image effect. Moreover, when the working-edge 440 extends from the distal end to the proximal end along K-direction, the distance between the working-edge 440 and the central axis of the transparent tip 450 is increasing, that is, the 2 working-edges 440 are gradually sloped outward from the distal end to the proximal end.

As described in the background, when passing the obturator through the cannula for the penetration, the penetration force is large. In the prior art, there are many structures or measures disclosed to reduce the penetration force of a bladeless obturator. However, it can be roughly summarized into two categories: the first type is adopting the completely symmetrical obturator and two or more working-edges; the second type is adopting the spear-shaped structure (i.e. the size in one direction is significantly smaller than the size in the other direction). Those skilled in the art should understand that the length of the distal-end portion of the obturator absolutely exceeds the total length of the distal end of the cannula, usually between 15 mm-25 mm, which is limited by the body wall and the body cavity structure and the clinical application. Therefore, it is not possible to adopt a single method of reducing the initial penetrating volume, for example, designing the spear-shaped obturator as a narrow and thin shape, although which is beneficial to reduce the force of penetrating the muscle or tissue, it will inevitably increase the subsequent tearing force and swelling force; and most of the time, the penetration, tearing, and swelling force are simultaneously present, and thus the effect of reducing the penetration force cannot be achieved.

As described in the background, when passing the obturator through the cannula for the penetration, the penetration force is large. In the prior art, there are many structures or measures disclosed to reduce the penetration force of a bladeless obturator. However, it can be roughly summarized into two categories: the first type is adopting the completely symmetrical obturator and two or more working-edges; the second type is adopting the spear-shaped structure (i.e. the size in one direction is significantly smaller than the size in the other direction). Those skilled in the art should understand that the length of the distal-end portion of the obturator absolutely exceeds the total length of the distal end of the cannula, usually between 15 mm-25 mm, which is limited by the body wall and the body cavity structure and the clinical application. Therefore, it is not possible to adopt a single method of reducing the initial penetrating volume, for example, designing the spear-shaped obturator as a narrow and thin shape, although which is beneficial to reduce the force of penetrating the muscle or tissue, it will inevitably increase the subsequent tearing force and swelling force; and most of the time, the penetration, tearing, and swelling force are simultaneously present, and thus the effect of reducing the penetration force cannot be achieved.

Based on the anatomy of the abdominal wall, the abdominal wall typically includes a skin layer, a fat layer, a muscle layer and a peritoneum from outside into the body. The skin has good elasticity and strength. When the penetration channel is established, the skin at the penetration site is usually cut first, and the incision is about 1.5 times wider than the maximum diameter of trocar, so the penetration and swelling resistance of the skin is not or very small when penetrating. The thickness of the peritoneum is relatively thin, about 1 mm diameter, and the thickness of the muscle layer is usually 10 to 15 mm. The thickness of the fat layer varies greatly depending on the degree of obesity, usually 15 to 40 mm. The fat layer is relatively loose, and the strength to penetrate and expand is moderate; the muscle layer is relatively dense, and the force of penetrating and expanding the muscle layer is relatively great; the peritoneal elasticity is better, and the force of penetrating and expanding the peritoneum is relatively great. The thickness and characteristics of the muscle layer indicate that the penetration force required to penetrate the muscle layer occupies a large proportion of the entire penetration force. The muscle layer is formed by a plurality of fibrous muscles wrapped by a fascia. It should be understood by those skilled in the art of human anatomy and materials science that the material of the abdominal wall (body wall) can be approximated as an elastic, anisotropic material with a certain incision sensitivity. When blunt object is penetrated into the abdominal wall through the skin incision, the abdominal wall manifests elastic elongation; when a sharp tip or thin-walled structure is penetrated through the skin incision into the abdominal wall, it is characterized by penetrating and tearing the fascia to separate muscle fibers instead of cutting muscle fibers; when applying a transverse-pulling-tearing force or an overall swelling force to the abdominal wall with the wound, the abdominal wall preferentially grows along the previous incision instead of creating a new incision from other locations. Those skilled with the anisotropy and sensitivity of the incision should be able to understand that one incision is made in one direction of the weaker strength of the anisotropic material, and then cut along the incision with a sharp edge and simultaneously applied perpendicularly to this direction. The tearing force produces a better cutting effect and requires minimal work or minimal force.

Figure 31:
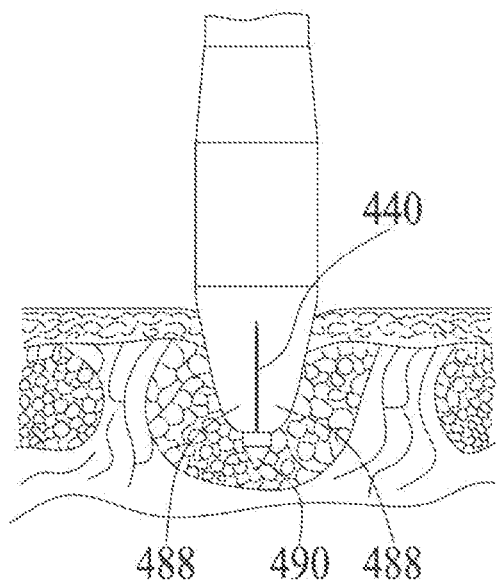
FIG. 31-33 is a simulated view of the distal-end portion of FIG. 27 in the clinical application.
Figure 32:
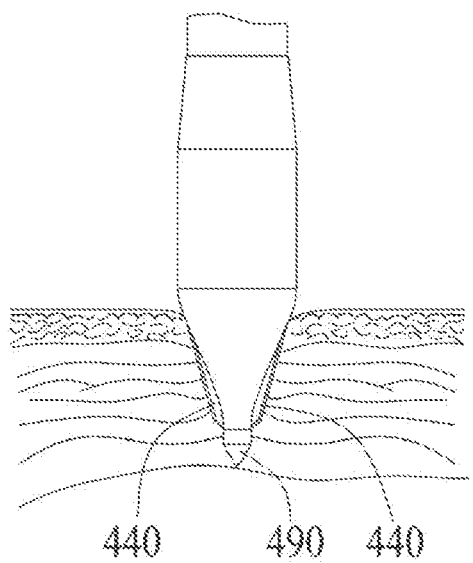
Figure 33:
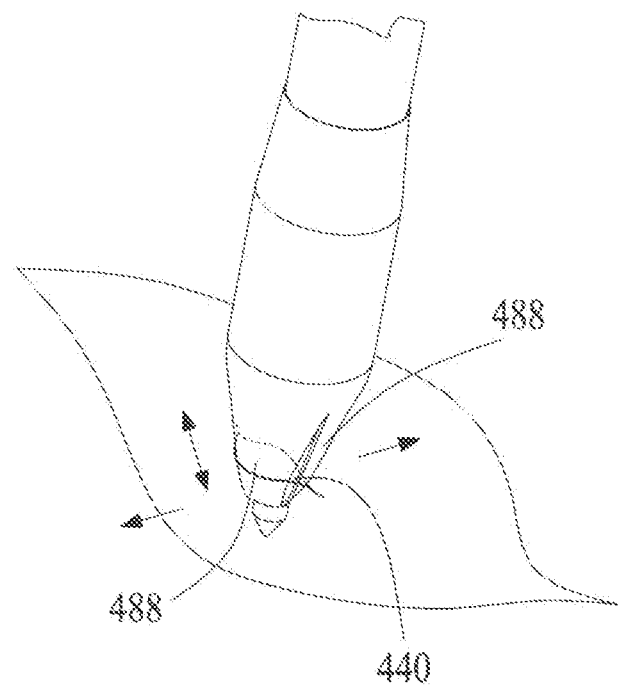

Referring to FIG. 31-33, the top-portion 490 facilitates penetration into the muscles (the abdominal wall), and the spear-portion 480 facilitates reducing the penetration volume, thereby reduce the penetration force. While the dimension of the first transverse-portion is larger than the dimension of the second transverse-portion, which includes two thin and sharp working edges 440; in the penetration, the blunt-separating portion 488 is generally perpendicular to the incision (or the muscle fibers) and the working-edge 440 is generally parallel to the incision (or the muscle fibers). The blunt-separating portion 488 produces a transverse-pulling-tearing force on the incision (the muscle fibers), while the working-edge 440 continues to cut and separate the incision (or the muscle fibers), thereby contributing to a greater reduction in penetration force. As the background says, surgeons are often used to penetrate into the body while rotating back and forth in a small range. While the back-forth rotation of the blunt-separating portion 488 when rotated back and forth gives the incision (or the muscle fibers) a greater transverse-tearing force, and the working-edge 440 is also cut and separated more smoothly along the incision (or between the muscle fibers).

Figure 34:
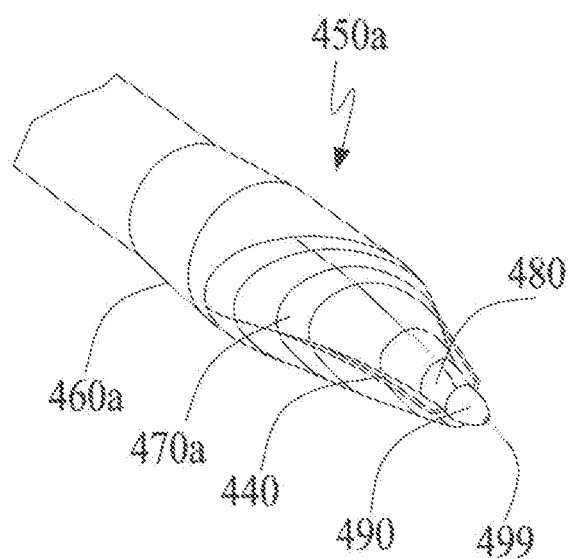
FIG. 34 is a side projection view of the distal-end portion in the fourth embodiment of the invention.
Figure 35:
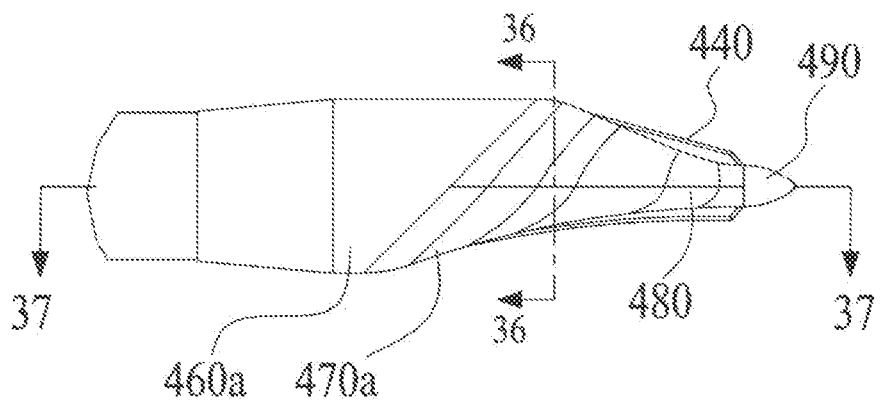
FIG. 35 is a side projection view of the distal-end portion in FIG. 34.
Figure 36:
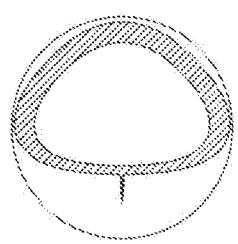
FIG. 36 is a cross-section view taken along line 36-36 of FIG. 34.
Figure 37:
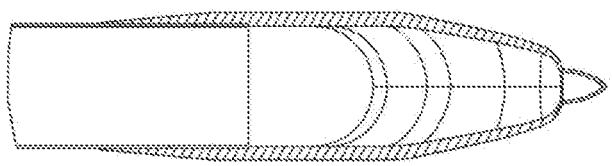
FIG. 37 is a cross-section view taken along line 37-37 of FIG. 34.
Figure 38:
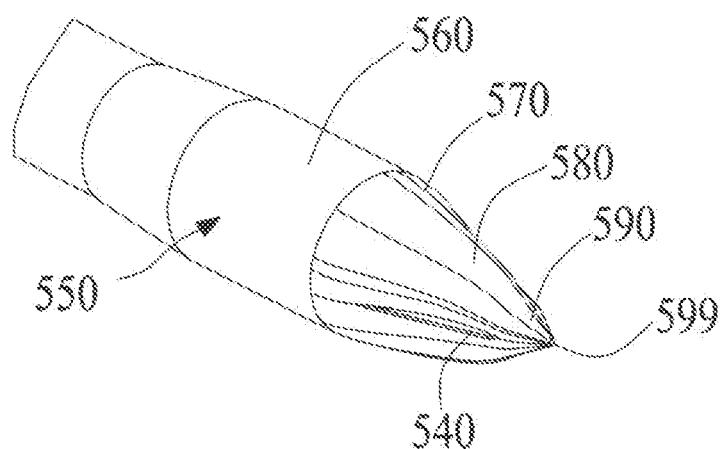
FIG. 38 is a 3D perspective view of the distal-end portion in the fifth embodiment of the invention.
Figure 39:
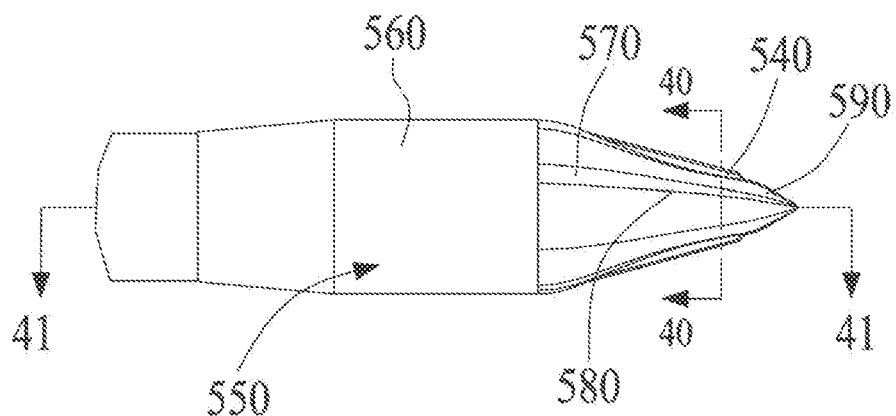
FIG. 39 is a side projection view of the distal-end portion in FIG. 38.
Figure 40:
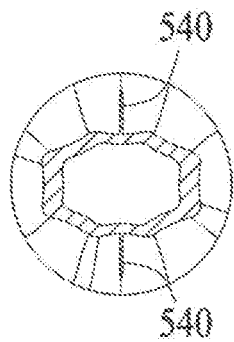
FIG. 40 is a cross-section view taken along line 40-40 of FIG. 38.
Figure 41:
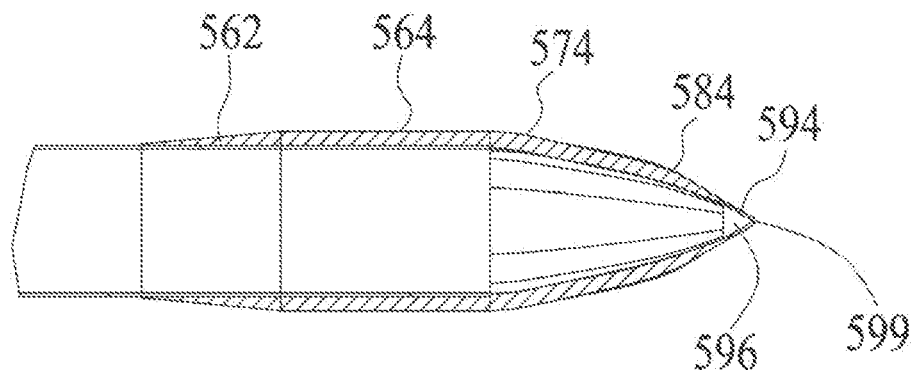
FIG. 41 is a cross-section view taken along line 41-41 of FIG. 38.

FIG. 34-37 show detailed depiction of the transparent bladeless obturator 450a in the fourth embodiment of the invention. The transparent tip 450a is divided into 4 portions, from the distal end to the proximal end, a top-portion 490, a spear-portion 480, a transition-portion 470a and a base-portion 460a. The numerical designations of the geometrical structure in FIG. 34-36 are the same as which in FIG. 27-30, it indicates that the structure of the same designations of the transparent tip 450a and the transparent tip 450 is basically equivalent. The transparent tip 450 includes a longitudinal axis (labeled as K-direction), the first transverse direction (labeled as M-direction) and the second transverse direction (labeled as N-direction), wherein the M-direction, the N-direction, and the K-direction are substantially perpendicular to each other. Moreover, the dimension of M-direction is larger than the dimension of N-direction in the spear-portion 480. Mainly referring to FIG. 35 and FIG. 36, the transition-portion 470a, the transition portion 470a is not only larger in the dimension of M-direction than in the N-direction, but also asymmetric in the N-direction relative to the M-direction. That is one side dimension of the N-direction is larger than the other side dimension. The transition-portion 470a facilitates reducing the force of the transition portion 470a to stretch the incision when the transparent tip 450a is inserted into the body wall.

FIG. 38-41 show detailed depiction of the transparent bladeless obturator 550 in the fifth embodiment of the invention. The transparent tip 550 is divided into 4 portions, from the distal end to the proximal end, a top-portion 590, a spear-portion 580, a transition-portion 570 and a base-portion 560. The top-portion 590 includes an apex 599, a rotary-wall 594 which extends from the apex 599 toward the proximal end and gradually increases, said rotary-wall 594 including a conical sweeping-wall, said rotary-wall 594 limiting the hollow cone 596. The transition-portion 570 includes a sweeping-wall 574 that is connected to a sweeping-wall 584 with smooth transition. The base-portion 560 includes a proximal beveled-wall 562 and a distal cylindrical-wall 564.

Referring to 38-41, the transparent tip 550 includes a longitudinal axis (labeled as K-direction), the first transverse direction (labeled as M-direction) and the second transverse direction (labeled as N-direction), wherein the M-direction, the N-direction, and the K-direction are substantially perpendicular to each other. The partial portion which the spear-portion 580 is connected to the top-portion 590 has a dimension in the M-direction that is larger than the dimension in the N-direction. From the distal end to the proximal end, the dimensions of M-direction and N-direction of the spear-portion 580 are simultaneously increased, and from the distal end to the proximal end the dimension ratio of the M-direction/N-direction is getting smaller and smaller. The partial portion which the transition-portion 570 is connected to the spear-portion 580 has a dimension in the M-direction that is larger than the dimension in the N-direction. From the distal end to the proximal end, the dimensions of M-direction and N-direction of transition-portion 570 are simultaneously increased, and from the distal end to the proximal end the dimension ratio of the M-direction and N-direction is getting smaller and smaller. The transparent tip includes two substantially symmetrical working edges 540. Mainly referring to FIG. 35 and FIG. 36, the cross-section disclosed in the present embodiment is a polygon, and the smooth transition of the top-portion 590 and the spear-portion 580 has no significant boundary. The transparent tip 550 has the advantage similar to the transparent tip 450.

Many different embodiments and examples of the invention have been shown and described. One ordinary skilled in the art will be able to make adaptations to the methods and apparatus by appropriate modifications without departing from the scope of the invention. For example, the endoscope lock mechanism disclosed in other inventions may be adapted to the lock structure. Or an endoscope is not used as a device for transmitting the light source and the image, but is replaced with a camera device with a similar function. Several modifications have been mentioned, to those skilled in the art, other modifications are also conceivable. Therefore, the scope of the invention should follow the additional claims, and at the same time, it should not be understood that it is limited by the specification of the structure, material or behavior illustrated and documented in the description and drawings.

What is claimed is:

1. An improved optical bladeless obturator comprises a proximal handle, a distal-end portion and a shaft there between, the handle and the shaft including a generally-aligned axis aperture, the distal-end portion including a transparent tip, wherein:
    a) the transparent tip comprising a top-portion, a spear-portion, a transition-portion and a base-portion;
    b) the top-portion includes an apex and a rotary-wall extending axially from the apex to a proximal end and shaping a hollow cone that is tapered toward the proximal end; the spear-portion including a sweeping-wall, the rotary-wall and the sweeping-wall extend to be intersected and form a circular field of vision;
    c) the sweeping-wall extends axially from a distal end to a proximal end and gradually increases in transverse wall thickness; the spear-portion includes a first transverse-portion and a second transverse-portion, and the first transverse-portion is wider and thicker than the second transverse-portion;
    d) a transverse dimension ratio of the first transverse-portion and the second transverse-portion gradually reducing from the distal end to the proximal end;

wherein the circular field of vision conforms to the following equation:

$$2\text{ mm} \leq D \leq 0.5 D_0$$

wherein:
D=diameter of the circular field of view
$D_0$=the maximum outer diameter of the distal-end portion of the obturator;
wherein the cross section of the spear-portion is an oval-shape or approximately an oval-polygon.

2. The obturator of claim 1, wherein the rotary-wall has a convex-shape, through the apex and the circular field of vision drawing a conical surface, the rotary-walls outside the conical surface.

3. The obturator of claim 1, inside the circular field of vision, the rotary-wall is axisymmetric and uniform in the thickness to reduce image differences.

4. The obturator of claim 3, outside the circular field of vision, the transparent tip contains a distorted or uneven geometry.

5. The obturator of claim 1, wherein the first transverse portion of the spear-portion extends transversely from the center to sides to form two substantially symmetrical and atraumatic blunt separating-portions.

6. The obturator of claim 5, wherein the transparent tip includes at least one thin working-edge, the working-edge extends transversely outward from the second transverse-portion.

7. The obturator of claim 6, wherein the working-edge is substantially perpendicular to the first transverse-portion.

8. The obturator of claim 7, wherein two working-edges extends outwardly from the outer surface of the spear-portion to the outer surface of the transition portion.

9. The obturator of claim 7, wherein the working-edge extends from the distal end to the proximal end, the distance between the working-edge and the central axis of the transparent tip is increasing.

10. The obturator of claim 7, wherein the blunt separating-portions are configured to produce a transverse-pulling-tearing force on the incision while the working-edges are configured to continue to cut and separate the incision, thereby contributing to reduction in penetration force.

11. The obturator of claim 1, wherein the transparent tip includes a longitudinal axis (labeled as K-direction), a first transverse direction (labeled as M-direction) and a second transverse direction (labeled as N-direction); the M-direction, the N-direction, and the K-direction are substantially perpendicular to each other; the dimension of M-direction is larger than the dimension of N-direction in the spear-portion.

12. The obturator of claim 11, wherein the transition-portion is not only larger in the dimension of M-direction than in the N-direction, but also asymmetric in the N-direction relative to the M-direction; one side dimension of the N-direction is larger than the other side dimension.

* * * * *